United States Patent
Shone et al.

(10) Patent No.: US 8,372,405 B2
(45) Date of Patent: Feb. 12, 2013

(54) PROTEINS WITH IMPROVED SOLUBILITY AND METHODS FOR PRODUCING AND USING SAME

(75) Inventors: Clifford C. Shone, Salisbury (GB); James A. Crawford, Hilliard, OH (US)

(73) Assignee: Health Protection Agency, Salisbury, Wiltshire (GB)

( * ) Notice: Subject to any disclaimer, the term of this patent is extended or adjusted under 35 U.S.C. 154(b) by 0 days.

(21) Appl. No.: 13/252,671

(22) Filed: Oct. 4, 2011

(65) Prior Publication Data

US 2012/0034239 A1 Feb. 9, 2012

Related U.S. Application Data

(63) Continuation of application No. 12/083,096, filed as application No. PCT/US2006/038757 on Oct. 5, 2006, now abandoned.

(60) Provisional application No. 60/724,274, filed on Oct. 7, 2005, provisional application No. 60/742,900, filed on Dec. 7, 2005.

(51) Int. Cl.
  *A61K 39/40* (2006.01)
(52) U.S. Cl. .................................................. 424/167.1
(58) Field of Classification Search ................ 424/167.1
  See application file for complete search history.

(56) References Cited

U.S. PATENT DOCUMENTS

| 5,874,238 | A | 2/1999 | Potempa et al. |
| 6,967,088 | B1 | 11/2005 | Williams et al. |
| 2004/0013687 | A1 | 1/2004 | Simpson et al. |
| 2007/0299008 | A1* | 12/2007 | Rummel ........................ 514/12 |

FOREIGN PATENT DOCUMENTS

| EP | 0355460 A | 2/1990 |
| WO | 9807864 | 2/1998 |
| WO | 0028041 | 5/2000 |

OTHER PUBLICATIONS

Baldwin et al. "The C-terminus for botulinum neurotoxin type A light chain contributes to solubility, catalysis, and stability" Protein Expression and Purification 37 (2004) pp. 187-195.*
Tsukamoto, et al. "2002 Sequence of the botulinum neurotoxin type E" Submitted (Mar. 2002) to the EMBL/GenBank/DDBJ databases.
Keller, et al. [1999] FEBS Letters, vol. 456, pp. 137-142.
Bowie, et al. [1990] Science 1990, 247:1306-1310.
European Search Report in Appln. No. 06816196.7 (EP National Stage of PCT/US06/38757) dated Sep. 18, 2009, 9 pages.
Foran, et al. [2002] Journal of Biological Chemistry, vol. 278, No. 2, pp. 1363-1371.

* cited by examiner

*Primary Examiner* — Gary Nickol
*Assistant Examiner* — Nina Archie
(74) *Attorney, Agent, or Firm* — Morris, Manning & Martin, LLP; Christopher W. Raimund

(57) ABSTRACT

A method is provided for improving the solubility of proteins, for example, bacterial toxins. In one embodiment, solubility is improved by introducing point mutations that replace cysteine residues capable of forming intermolecular disulfide bonds with other amino acid residues that do not form such bonds. By abrogating the ability of the cysteine residues to form inter-molecular disulfide bonds, aggregation of the protein is reduced, thereby improving the solubility of the protein. In another embodiment, solubility of the protein is improved by producing truncated forms of the protein that express the LHN domain and a fragment of the Hc domain. Proteins made according to the method of the invention are useful, for example, as immunodiagnostic agents and vaccine components.

12 Claims, 6 Drawing Sheets

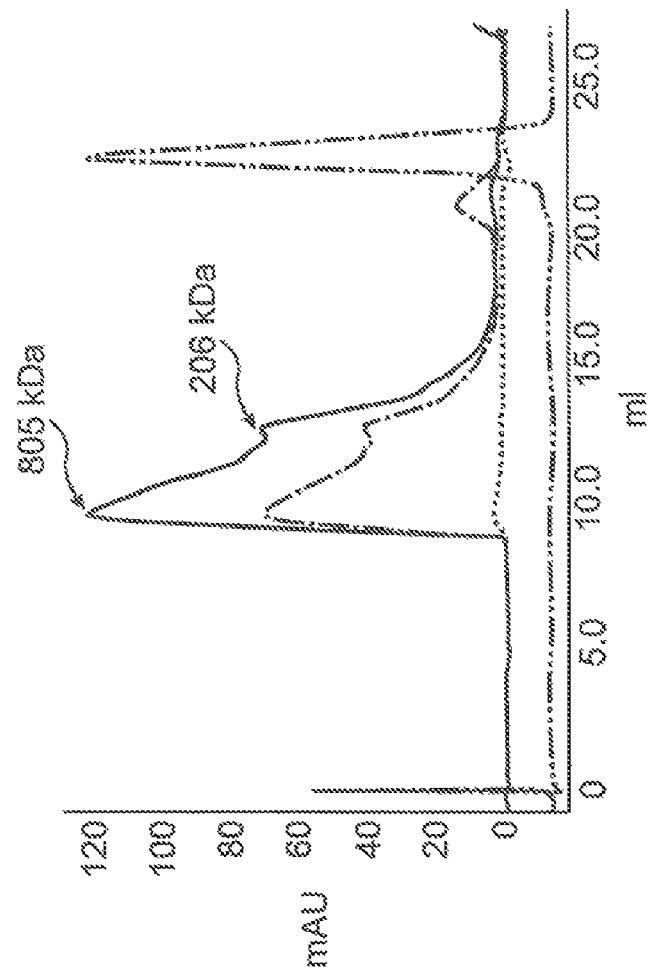

| LANE | SAMPLE | REDUCTANT |
|---|---|---|
| 1 | MW MARKER | NA |
| 2 | LHn-E C26S | + |
| 3 | LHn-E C26S | - |
| 4 | LHn-E C347S | + |
| 5 | LHn-E C347S | - |
| 6 | LHn-E C26S+C347S | + |
| 7 | LHn-E C26S+C347S | - |
| 8 | NATIVE LHn-E | + |
| 9 | NATIVE LHn-E | - |

PROTEINS WITH IMPROVED SOLUBILITY AND METHODS FOR PRODUCING AND USING SAME

CROSS REFERENCE TO RELATED APPLICATIONS

This application is a continuation of U.S. patent application Ser. No. 12/083,096, pending, which is a national stage of PCT/US2006/038757, filed on Oct. 5, 2006, and which claims the benefit of United States provisional application nos. 60/724,274, filed Oct. 7, 2005, and 60/742,900, filed Dec. 7, 2005, the entire disclosures of which are incorporated herein by reference.

DESCRIPTION OF THE INVENTION

Field of the Invention

The present invention relates to methods for producing recombinant proteins that exhibit improved utility and process characteristics, such as solubility, compared to the corresponding native proteins. The invention also relates to proteins made according to the present methods, nucleic acids encoding the proteins, and the use of the proteins for prophylactic and therapeutic applications.

Background of the Invention

Proteins produced by organisms, and in particular microorganisms such as bacteria, are of interest because of their potential to serve as immunodiagnostic reagents, therapeutic agents, and vaccine components. Toxins are one group of proteins that have been extensively investigated for those purposes. It is often desirable, if not necessary, to purify proteins to remove contaminating materials that render them unsuitable for those uses. However, some proteins will form aggregates during purification. Aggregates tend to exhibit low solubility and other characteristics that are undesirable, such as low immunogenicity. In some cases, aggregates arise when cysteine residues in the protein of interest form aberrant intermolecular and/or intra-molecular disulfide bonds.

One family of bacterial toxins of interest as immunodiagnostic reagents, therapeutic agents, and vaccine components are the clostridial neurotoxins, such as those from *Clostridium botulinum* and *Clostridium butyricum*. Botulinum neurotoxin (BoNT) is one of the most potent toxins known to man. Its ingestion or inhalation inhibits neurotransmitter release from synaptic vesicles, resulting in neuroparalysis and death. The use of *Clostridium botulinum* neurotoxins as vaccine components is disclosed in U.S. Pat. No. 5,919,665 to J. A. Williams, which is incorporated by reference into this application. In addition, U.S. Pat. No. 6,051,239 to Simpson et al., U.S. Pat. No. 6,287,566 to M. T. Dertzbaugh, and U.S. Pat. No. 6,461,617 to Shone et al, each of which is incorporated by reference into this application, disclose the use of fragments of clostridial neurotoxin as vaccine components.

Seven serologically distinct forms of clostridial neurotoxin exist: types A, B, C, D, E, F, and G. Full length neurotoxin type E, for example, is designated BoNT/E. Each neurotoxin type shares a common architecture in which a catalytic L-chain (LC, ~50 kDa) is disulfide linked to a receptor binding and translocating H-chain (HC, ~100 kDa). The HC polypeptide comprises all or part of two distinct functional domains. The carboxy-terminal half of the HC (~50 kDa), termed the $H_C$ domain, is involved in the high affinity, neurospecific binding of the neurotoxin to cell surface receptors on the target neuron. The amino-terminal half, termed the $H_N$ domain (~50 kDa), mediates the translocation of at least some portion of the neurotoxin across cellular membranes such that the functional activity of the LC is expressed within the target cell. Although the heavy chain is required for BoNT to bind and enter the target cell, it is not toxic by itself.

One particular fragment of interest is the $LH_N$ fragment, such as the $LH_N$ fragment of neurotoxin E ($LH_N/E$). $LH_N/E$ corresponds to the first 845 N-terminal amino acid residues of the full length botulinum (or butyricum) neurotoxin E. It includes the LC and $H_N$ domains. During in vivo expression, as well as during purification, both recombinant $LH_N/E$ ($rLH_N/E$) and native forms of $LH_N/E$ form aggregates having a molecular mass ranging from about 120 kD to several million kD. Often $LH_N/E$ aggregates having masses of about 200 kD, 300 kD, 400 kD, 500 kD, 600 kD, 700 kD, and 800 kD are observed. Although aggregated $rLH_N/E$ can be recovered from insoluble lysate material by detergent extraction/reductant treatment and further purified (~90%) by anion exchange (Q Sepharose) and gel filtration (Superdex 200) chromatography, the recovered aggregate has undesirable properties. For example, purified aggregated $rLH_N/E$ is recognized in a conformation sensitive ELISA to a much lesser degree (~5-10-fold) compared to the native BoNT/E control, indicating that conformational epitopes are absent and/or buried within the aggregate. Further, animal efficacy data indicate that immunization with aggregated $LH_N/E$ does not protect animals against BoNT/E toxin challenge. Because conformational epitopes are known to play a key role in eliciting protective antibody responses, these results were not totally unexpected.

Different fermentation conditions, for example, slow initial growth, less potent inducers, and/or reduced induction temperatures, as well as different detergent extraction/reductant treatments and denaturation (e.g. urea)/refolding methodologies have been being explored in an effort to produce soluble, non-aggregated or less aggregated $LH_N/E$, but with limited success. Hence, there is a need for protein toxins and toxin subfragments, such as $LH_N/E$, that exhibit little or no aggregation and retain conformational epitopes that permit use of the toxins as immunodiagnostic reagents and vaccine components.

SUMMARY OF THE INVENTION

An object of the invention is to provide a method for reducing or preventing aggregate formation during purification and/or formulation of proteins, such as toxins and toxin fragments.

Another object of the invention is to provide greater batch-to-batch consistency within protein products when characterized by standard methods of protein analysis.

Still another object of the invention is to provide proteins with improved solubility and process characteristics.

Yet another object of the invention is to provide toxin proteins and toxin fragments with improved solubility and process characteristics for use as immunodiagnostic reagents, therapeutic agents, and vaccine components.

Additional objects and advantages of the invention will be set forth in part in the description that follows, and in part will be obvious from the description, or may be learned by practice of the invention. The objects and advantages of the invention will be realized and attained by the compositions and methods particularly pointed out in the appended claims.

To achieve the objects and in accordance with the purpose of the invention, as embodied and broadly described herein, the disclosure describes in one embodiment a recombinant protein comprising at least one point mutation that substitutes a cysteine residue with another amino acid residue, wherein said substitution improves the solubility of the recombinant protein. In some embodiments, the protein is a toxin, such as a bacterial toxin, or a fragment thereof. The toxin may be a neurotoxin or neurotoxin fragment from, for example, *Clostridium botulinum* or *Clostridium butyricum*. In certain embodiments, the toxin is a clostridial neurotoxin, such as neurotoxin E, or a fragment thereof, such as an $LH_N/E$ fragment.

The disclosure also provides toxin fragments that are more soluble than certain other fragments. For example, in some embodiments, the toxin is a clostridial neurotoxin and the fragment is an $LH_N$ fragment that further comprises amino acid sequences from the $H_C$ fragment, wherein the resulting $LH_N+H_C$ fragment is more soluble than the $LH_N$ fragment. In certain embodiments, these fragments are recombinant neurotoxin E fragments.

The invention also comprises nucleic acids encoding the recombinant proteins set forth in the disclosure, vectors comprising those nucleic acid sequences, and methods of expressing the encoded proteins in host cells.

In yet other embodiments, the invention encompasses methods used in improving the solubility and process characteristics of the toxin and toxin fragments described in the specification.

The invention further comprises methods of using the disclosed toxin and toxin fragments as therapeutic agents and vaccine components.

Thus, the invention, provides the following embodiments:

In one embodiment, then invention provides a recombinant protein comprising at least one point mutation that substitutes a cysteine residue with another amino acid residue, wherein said substitution improves the solubility of the recombinant protein.

In another embodiment, the protein is a toxin or non-toxic derivative of a toxin.

Still other embodiments of the invention encompass a toxin or non-toxic derivative of a toxin that is of bacterial origin.

In other embodiments, the bacterial toxin or toxin derivative is from either *Clostridium botulinum* or *Clostridium butyricum*.

In yet other embodiments, the toxin is a neurotoxin or neurotoxin derivative.

In still other embodiments, the neurotoxin is neurotoxin A, B, C, D, E, F, or G, or a non-toxic derivative thereof.

In yet other embodiments, the neurotoxin or non-toxic derivative is a fragment of neurotoxin E.

In other embodiments the fragment is the $LH_N/E$ fragment of neurotoxin E.

In still other embodiments, the neurotoxin E fragment comprises, at least one cysteine to serine amino acid substitution.

In yet other embodiments, the substitution of serine for cysteine occurs at amino acid residue 26, amino acid residue 347, or both amino acid residue 26 and amino acid residue 347 compared to the $LH_N$ fragment of SEQ ID NO: 1 or SEQ ID NO: 2.

The invention includes embodiments in which a protein of the invention has active endopeptidase activity.

The invention also includes embodiments in which a protein of the invention has attenuated endopeptidase activity.

Among other embodiments, the invention also includes nucleic acids encoding a recombinant protein of the invention.

Similarly, other embodiments of the invention include a method for improving the solubility of a protein having at least one cysteine residue that forms an intermolecular disulfide bond, comprising:
(a) providing a nucleic acid sequence encoding a recombinant protein comprising at least one cysteine residue;
(b) introducing at least one point mutation into the nucleic acid sequence that substitutes at least one cysteine residue with another amino acid residue;
(c) transforming a host cell with the mutated nucleic acid sequence; and
(d) expressing the nucleic acid sequence to produce the protein.

In some embodiments, the protein in the method is a toxin or non-toxic derivative thereof.

In other embodiments, the protein in the method is a toxin or non-toxic derivative of bacterial origin.

In yet other embodiments, the protein in the method is a bacterial toxin or toxin derivative from either *Clostridium botulinum* or *Clostridium butyricum*.

In still other embodiments, the protein in the method is a toxin a neurotoxin or neurotoxin derivative.

In some embodiments, the neurotoxin in the method is neurotoxin A, B, C, D, E, F, or G, or a non-toxic derivative thereof.

In other embodiments, the non-toxic derivative in the method is a is a fragment of neurotoxin E.

In yet other embodiments, the fragment in the method is the $LH_N/E$ fragment of neurotoxin E.

In some embodiments of the method, the amino acid introduced by the at least one point mutation is a serine.

In other embodiments of the method, the protein is a $LH_N$ fragment of clostridial neurotoxin E and the at least one point mutation substitutes a serine for a cysteine at amino acid residue 26, amino acid residue 347, or both amino acid residue 26 and amino acid residue 347 compared to the $LH_N$ fragment of SEQ ID NO: 1 or SEQ ID NO: 2.

In still other embodiments of the method, the point mutation is introduced by site-directed mutagenesis.

Various embodiments of the method further comprise isolating the protein.

In certain embodiments of the method, the host cell is a mammalian, plant, insect, fungal, or bacterial cell.

The methods of the invention include embodiments in which a protein of the invention has active endopeptidase activity.

The methods of the invention also include embodiments in which a protein of the invention has attenuated endopeptidase activity.

In some embodiments, the invention provides for the use of a protein of the invention for the manufacture of a medicament for the treatment or prevention of botulism.

Other embodiments of the invention include compositions comprising a protein of the invention and a pharmaceutically acceptable carrier.

In still other embodiments, the invention provides methods of protecting an individual from botulism, comprising administering to the individual a composition of the invention.

Yet other embodiments of the invention provide a method of producing antibodies that neutralize a clostridial neurotoxin, comprising administering a composition of the invention to an animal, allowing the animal to develop neutralizing antibodies to the clostridial neurotoxin, and isolating an antiserum that neutralizes the clostridial neurotoxin from the animal.

Other embodiments encompass an antiserum produced by a method of the invention.

In still other embodiments, the invention provides methods of treating exposure to a clostridial neurotoxin, comprising administering to a patient that has been exposed to the clostridial neurotoxin an antiserum of the invention.

In other embodiments, the invention provides a recombinant protein comprising a truncated botulinum serotype E toxin, wherein the truncation improves the solubility of the recombinant protein.

In some embodiments, the protein comprises a truncation in the Hc domain.

In other embodiments, the truncated protein comprises the $LH_N/E$ domain and the amino terminal 103 amino acids of the Hc domain.

Still other embodiments of the invention encompass a truncated protein comprising the amino terminal 948 amino acids of the serotype E toxin.

In yet other embodiments, the truncated protein comprises the $LH_N/E$ domain and the amino terminal 202 amino acids of the Hc domain.

Still other embodiments of the invention encompass a truncated protein comprising the amino terminal 1047 amino acids of the serotype E toxin.

In other embodiments, the truncated protein comprises the $LH_N/E$ domain and the amino terminal 304 amino acids of the Hc domain.

Still other embodiments of the invention encompass a truncated protein comprising the amino terminal 1149 amino acids of the serotype E toxin.

Additional embodiments of the invention include nucleic acids encoding a truncated botulinum serotype E toxin.

In still other embodiments, the invention provides methods for improving the solubility of a clostridial neurotoxin, comprising:
(a) providing a nucleic acid sequence encoding a clostridial neurotoxin;
(b) modifying the nucleic acid sequence so that it encodes the $LH_N$ fragment and a portion of the $H_C$ fragment of the neurotoxin;
(c) transforming the modified nucleic acid sequence into a host cell capable of expressing the modified nucleic acid sequence; and
(d) expressing the modified nucleic acid sequence to produce the protein.

In yet other embodiments, the invention provides for use of a truncated botulinum serotype E toxin for the manufacture of a medicament for the treatment or prevention of botulism.

In other embodiments, the invention provides a composition comprising a truncated botulinum serotype E toxin and a pharmaceutically acceptable carrier.

In still other embodiments, the invention provides a method of protecting an individual from botulism, comprising administering to the individual a composition comprising a truncated botulinum serotype E toxin and a pharmaceutically acceptable carrier.

Other embodiments of the invention include a method of producing antibodies that neutralize a clostridial neurotoxin, comprising administering a composition comprising a truncated botulinum serotype E toxin and a pharmaceutically acceptable carrier to an animal, allowing the animal to develop neutralizing antibodies to the clostridial neurotoxin, and isolating an antiserum that neutralizes the clostridial neurotoxin from the animal.

In still other embodiments, the invention provides an antiserum produced by the method of the preceding paragraph.

In yet other embodiment, the invention provides methods of treating exposure to a clostridial neurotoxin, comprising administering to a patient that has been exposed to the clostridial neurotoxin an antiserum of the invention.

In yet another embodiment, the invention provides a mutated botulinum serotype E toxin comprising either or both of a leucine residue substituted for the tryptophan residue at position 1223 and a phenylalanine residue for the tyrosine residue at position 1224 of SEQ ID NO: 1 or SEQ ID NO: 2.

The invention also provides, in additional embodiments, for the use of a protein of the preceding paragraph for the manufacture of a medicament for the treatment or prevention of botulism.

In still other embodiments, the invention provides an in vitro method for improving the solubility of a protein having at least one cysteine residue that forms an intermolecular disulfide bond, comprising:
(a) providing a nucleic acid sequence encoding a recombinant protein comprising at least one cysteine residue;
(b) introducing at least one point mutation into the nucleic acid sequence that substitutes at least one cysteine residue with another amino acid residue;
(c) transforming a host cell with the mutated nucleic acid sequence; and
(d) expressing the nucleic acid sequence to produce the protein.

Yet other embodiments of the invention encompass an in vitro method for improving the solubility of a clostridial neurotoxin, comprising:
(a) providing a nucleic acid sequence encoding a clostridial neurotoxin;
(b) modifying the nucleic acid sequence so that it encodes the $LH_N$ fragment and a portion of the $H_C$ fragment of the neurotoxin;
(c) transforming the modified nucleic acid sequence into a host cell capable of expressing the modified nucleic acid sequence; and
(d) expressing the modified nucleic acid sequence to produce the protein.

In still other embodiments, the invention provides a method of producing antibodies that neutralize a clostridial neurotoxin, comprising isolating antibodies elicited by an inoculated polypeptide, wherein said polypeptide is a protein according to the invention.

Yet other embodiments of the invention provided for the use of an antiserum of the invention for the manufacture of a medicament for treating exposure to clostridial neurotoxin.

It is to be understood that both the foregoing general description and the following detailed description are exemplary and explanatory only and are not restrictive of the invention, as claimed. The accompanying drawings illustrate embodiments of the invention and together with the description, serve to explain the principles of the invention.

BRIEF DESCRIPTION OF THE DRAWINGS

FIGS. 1A and 1B are a polyacrylamide gel and chromatogram, respectively, showing production of recombinant $LH_N/E$ in *Escherichia coli* as a high molecular weight aggregate.

DESCRIPTION OF THE EMBODIMENTS

Figures 2A, 2B:
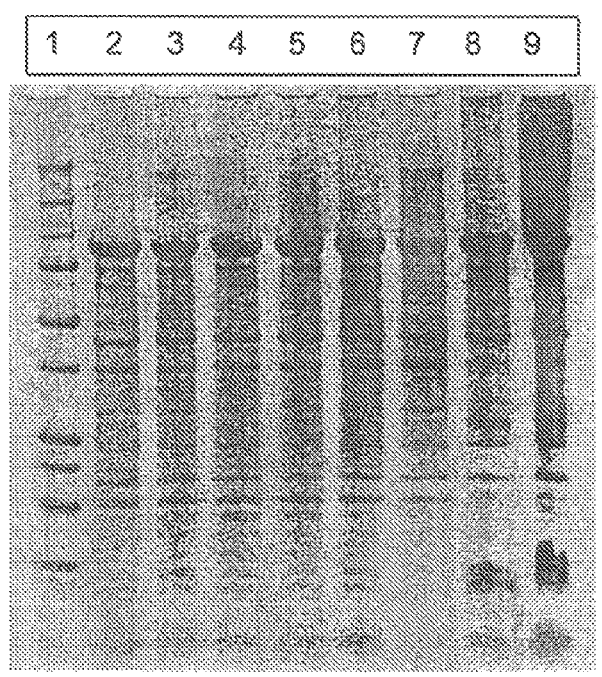
FIGS. 2A and 2B demonstrate high levels of mutated recombinant $LH_N/E$ in *Escherichia coli* as non-aggregated proteins.

The section headings used herein are for organizational purposes only and are not to be construed as limiting the subject matter described. All documents, or portions of documents, cited herein, including but not limited to patents, patent applications, articles, books, and treatises, are hereby expressly incorporated by reference in their entirety for any purpose. In the event that one or more of the incorporated documents or portions of documents defines a term that contradicts that term's definition in the application, this application controls.

The use of the singular includes the plural unless specifically stated otherwise. The word "a" or "an" means "at least one" unless specifically stated otherwise. The use of "or" means "and/or" unless stated otherwise. The meaning of the phrase "at least one" is equivalent to the meaning of the phrase "one or more." Furthermore, the use of the term "including," as well as other forms, such as "includes" and "included," is not limiting. Also, terms such as "element" or "component" encompass both elements or components comprising one unit and elements or components comprising more than one unit unless specifically stated otherwise.

Neurotoxic proteins and fragments of these proteins are important immunodiagnostic reagents, therapeutic agents, and vaccine components. Functional neurotoxins are hazardous to work with, however, so investigators prefer to use recombinant proteins that have been genetically modified to reduce or eliminate their neurotoxicity. Unfortunately, it can be difficult to purify some of the recombinant, non-toxic, proteins because they often form aggregates, which have reduced solubility and are less effective reagents for use in immunodiagnostic, therapeutic, and vaccine applications. For example, although aggregated rLH$_N$/E can be purified, it is recognized in a conformation-sensitive ELISA to a much lesser degree (~5-10-fold) than is the native BoNT/E toxin, indicating that conformational epitopes are absent and/or buried within the aggregate. Also, immunization with aggregated LH$_N$/E does not protect animals against BoNT/E toxin challenge.

Accordingly, the disclosure provides recombinant proteins with improved solubility. For example, in one embodiment, the disclosure describes a recombinant protein comprising at least one point mutation that substitutes, a cysteine residue with another amino acid residue, wherein said substitution improves the solubility of the recombinant protein. In some embodiments, the protein is a toxin, such as a bacterial toxin, for example, a neurotoxin or neurotoxin fragment from *Clostridium botulinum* or *Clostridium butyricum*. In some embodiments, the protein is a fragment of a neurotoxin, such as an LH$_N$ fragment, for example, an LH$_N$/E fragment. In certain embodiments, the first and third cysteine residues, counting from the amino terminus of a naturally-occurring neurotoxin amino acid sequence, have been replaced with non-cysteine amino acids, such as serine, in the recombinant neurotoxin protein or fragment thereof. Although mutations in clostridial neurotoxin E are exemplified, clostridial neurotoxins A, B, C, D, F, and G can be modified in the same manner.

Nucleic acid sequences encoding various neurotoxins have been cloned and those nucleic acid sequences are known in the art. For example, a nucleic acid sequence of a full length neurotoxin E from *C. botulinum* is provided in GenBank accession no. AB082519. A nucleic acid sequence of a full length neurotoxin E from *C. butyricum* is provided in GenBank accession no. AB088207.

An example of an amino acid sequence of *C. botulinum* BoNT/E neurotoxin is:

```
                                                       (SEQ ID NO: 1)
MPKINSFNYN DPVNDRTILY IKPGGCQEFY KSFNIMKNIW IIPERNVIGT

TPQDFHPPTS LKNGDSSYYD PNYLQSDEEK DRFLKIVTKI FNRINNNLSG

GILLEELSKA NPYLGNDNTP DNQFHIGDAS AVEIKFSNGS QDILLPNVII

MGAEPDLFET NSSNISLRNN YMPSNHRFGS IAIVTFSPEY SFRFNDNCMN

EFIQDPALTL MHELIHSLHG LYGAKGITTK YTITQKQNPL ITNIRGTNIE

EFLTFGGTDL NIITSAQSND IYTNLLADYK KIASKLSKVQ VSNPLLNPYK

DVFEAKYGLD KDASGIYSVN INKFNDIFKK LYSFTEFDLR TKFQVKCRQT

YIGQYKYFKL SNLLNDSIYN ISEGYNINNL KVNFRGQNAN LNPRIITPIT

GRGLVKKIIR FCKNIVSVKG IRKSICIEIN NGELFFVASE NSYNDDNINT

PKEIDDTVTS NNNYENDLDQ VILNFNSESA PGLSDEKLNL TIQNDAYIPK

YDSNGTSDIE QHDVNELNVF FYLDAQKVPE GENNVNLTSS IDTALLEQPK

IYTFFSSEFI NNVNKPVQAA LFVSWIQQVL VDFTTEANQK STVDKIADIS

IVVPYIGLAL NIGNEAQKGN FKDALELLGA GILLEFEPEL LIPTILVFTI

KSFLGSSDNK NKVIKAINNA LKERDEKWKE VYSFIVSNWM TKINTQFNKR

KEQMYQALQN QVNAIKTIIE SKYNSYTLEE KNELTNKYDI KQIENELNQK
```

-continued

```
VSIAMNNIDR FLTESSISYL MKIINEVKIN KLREYDENVK TYLLNYIIQH

GSILGESQQE LNSMVTDTLN NSIPFKLSSY TDDKILISYF NKFFKRIKSS

SVLNMRYKND KYVDTSGYDS NININGDVYK YPTNKNQFGI YNDKLSEVNI

SQNDYIIYDN KYKNFSISFW VRIPNYDNKI VNVNNEYTII NCMRDNNSGW

KVSLNHNEII WTFEDNRGIN QKLAFNYGNA NGISDYINKW IFVTITNDRL

GDSKLYINGN LIDQKSILNL GNIHVSDNIL FKIVNCSYTR YIGIRYFNIF

DKELDETEIQ TLYSNEPNTN ILKDFWGNYL LYDKEYYLLN VLKPNNFIDR

RKDSTLSINN IRSTILLANR LYSGIKVKIQ RVNNSSTNDN LVRKNDQVYI

NFVASKTHLF PLYADTATTN KEKTIKISSS GNRFNQVVVM NSVGNCTMNF

KNNNGNNIGL LGFKADTVVA STWYYTHMRD HTNSNGCFWN FISEEHGWQE

K.
```

This sequence includes the Met at residue 1. SEQ ID NO: 1 is the reference sequence for all numbering regarding *C. botulinum* BoNT/E and fragments thereof used in this specification, irrespective of whether those sequences have or do not have the first Met. The LH$_N$/E fragment extends from the amino terminus to amino acid residue 845 (Lys) in SEQ ID NO: 1.

An example of an amino acid sequence of *C. butryicum* BoNT/E neurotoxin is:

```
                                                (SEQ ID NO: 2)
MPTINSFNYN DPVNNRTILY IKPGGCQQFY KSFNIMKNIW IIPERNVIGT

IPQDFLPPTS LKNGDSSYYD PNYLQSDQEK DKFLKIVTKI FNRINDNLSG

RILLEELSKA NPYLGNDNTP DGDFIINDAS AVPIQFSNGS QSILLPNVII

MGAEPDLFET NSSNISLRNN YMPSNHGFGS IAIVTFSPEY SFRFKDNSMN

EFIQDPALTL MHELIHSLHG LYGAKGITTK YTITQKQNPL ITNIRGTNIE

EFLTFGGTDL NIITSAQSND IYTNLLADYK KIASKLSKVQ VSNPLLNPYK

DVFEAKYGLD KDASGIYSVN INKFNDIFKK LYSFTEFDLA TKFQVKCRQT

YIGQYKYFKL SNLLNDSIYN ISEGYNINNL KVNFRGQNAN LNPRIITPIT

GRGLVKKIIR FCKNIVSVKG IRKSICIEIN NGELFFVASE NSYNDDNINT

PKEIDDTVTS NNNYENDLDQ VILNFNSESA PGLSDEKLNL TIQNDAYIPK

YDSNGTSDIE QHDVNELNVF FYLDAQKVPE GENNVNLTSS IDTALLEQPK

IYTFFSSEFI NNVNKPVQAA LFVGWIQQVL VDFTTEANQK STVDKIADIS

IVVPYIGLAL NIGNEAQKGN FKDALELLGA GILLEFEPEL LIPTILVFTI

KSFLGSSDNK NKVIKAINNA LKERDEKWKE VYSFIVSNWM TKINTQFNKR

KEQMYQALQN QVNALKAIIE SKYNSYTLEE KNELTNKYDI EQIENELNQK

VSIAMNNIDR FLTESSISYL MKLINEVKIN KLREYDENVK TYLLDYIIKH

GSILGESQQE LNSMVIDTLN NSIPFKLSSY TDDKILISYF NKFFKRIKSS

SVLNMRYKND KYVDTSGYDS NININGDVYK YPTNKNQFGI YNDKLSEVNI

SQNDYIIYDN KYKNFSISFW VRIPNYDNKI VNVNNEYTII NCMRDNNSGW

KVSLNHNEII WTLQDNSGIN QKLAFNYGNA NGISDYINKW IFVTITNDRL

GDSKLYINGN LIDKKSILNL GNIHVSDNIL FKIVNCSYTR YIGIRYFNIF

DKELDETEIQ TLYNNEPNAN ILKDFWGNYL LYDKEYYLLN VLKPNNFINR
```

-continued
```
RTDSTLSINN IRSTILLANR LYSGIKVKIQ RVNNSSTNDN LVRKNDQVYI

NFVASKTHLL PLYADTATTN KEKTIKISSS GNRFNQVVVM NSVGNCTMNF

KNNNGNNIGL LGFKADTVVA STWYYTHMRD NTNSNGFFWN FISEEHGWQE

K.
```

This sequence includes the Met at residue 1. SEQ ID NO: 2 is the reference sequence for all numbering regarding *C. butyricum* BoNT/E and fragments thereof used in this specification, irrespective of whether those sequences have or do not have the first Met. The LH$_N$/E fragment extends from the amino terminus to amino acid residue 845 (Lys) in SEQ ID NO: 2.

In the case of neurotoxin proteins from *C. botulinum* and *C. butyricum*, any amino acid sequences disclosed in which the initial methionine is not included are also considered BoNT/E or LH$_N$/E fragments, as appropriate, even though the numbering of the amino acid residues in that particular fragment assumes the Met at position 1.

BoNT/E and fragments thereof that have endopeptidase activity have a glutamate (E) at position 213 and a histidine (H) at position 216. The endopeptidase activity can be abolished by mutating these sequences. For example, the specification describes BoNT/E and fragments thereof in which the glutamate is replaced with glutamine (Q) (i.e., E213Q) and the histidine is replaced with a tyrosine (Y) (i.e., H216Y). These proteins lack endopeptidase activity.

Examples of recombinant proteins comprising at least one point mutation that substitutes a cysteine residue with another amino acid residue, wherein said substitution improves the solubility of the recombinant protein include, but are not limited to:

a) a protein comprising residues 2 to 845 of the amino acid sequence set forth in SEQ ID NO: 1, wherein the cysteine at position 26 of SEQ ID NO: 1 is replaced with a serine;

b) a protein comprising residues 2 to 845 of the amino acid sequence set forth in SEQ ID NO: 1, wherein the cysteine at position 347 of SEQ ID NO: 1 is replaced with a serine;

c) a protein comprising residues 2 to 845 of the amino acid sequence set forth in SEQ ID NO: 1, wherein the cysteine at position 26 and the cysteine at position 347 of SEQ ID NO: 1 are each replaced with a serine;

d) a protein comprising residues 2 to 845 of the amino acid sequence set forth in SEQ ID NO: 2, wherein the cysteine at position 26 of SEQ ID NO: 2 is replaced with a serine;

e) a protein comprising residues 2 to 845 of the amino acid sequence set forth in SEQ ID NO: 2, wherein the cysteine at position 347 of SEQ ID NO: 2 is replaced with a serine; and f) a protein comprising residues 2 to 845 of the amino acid sequence set forth in SEQ ID NO: 2, wherein the cysteine at position 26 and the cysteine at position 347 of SEQ ID NO: 2 are each replaced with a serine.

In alternative embodiments, each of the proteins described in parts (a)-(f) of the preceding paragraph may consist of, rather than comprise, the respective amino acid sequences. Optionally, each of the proteins described in parts (a)-(f) of the preceding paragraph may further comprise a methionine at their respective amino termini. The solubility, immunogenicity, or both solubility and immunogenicity of the proteins described in parts (a)-(f) of the preceding paragraph is improved compared to proteins comprising or consisting of the corresponding amino acid sequence lacking the mentioned cysteine to serine replacement(s). In some embodiments, the proteins contain the E213Q and H216Y point mutations that abolish endopeptidase activity.

Additional examples of BoNT/E proteins or fragments thereof comprising Cys to Ser replacements are set forth in SEQ ID NOS: 7-14.

The disclosure also provides recombinant neurotoxins fragments that are more soluble than certain other fragments. For example, in some embodiments, the fragment is an LH$_N$ fragment that further comprises amino acid sequences from the H$_C$ fragment, wherein the resulting LH$_N$+H$_C$ fragment is more soluble than the LH$_N$ fragment. In certain embodiments, the LH$_N$ fragment is an LH$_N$/E fragment and the H$_C$ fragment is an H$_C$/E fragment. The LH$_N$ fragment may optionally comprise at least one point mutation that substitutes a cysteine residue with another amino acid residue.

Examples of recombinant neurotoxins fragments that are more soluble than certain other fragments include, but are not limited to:

a) a protein comprising residues 2 to 948 of the amino acid sequence set forth in SEQ ID NO: 1;

b) a protein comprising residues 2 to 1047 of the amino acid sequence set forth in SEQ ID NO: 1;

c) a protein comprising residues 2 to 1149 of the amino acid sequence set forth in SEQ ID NO: 1;

d) a protein comprising residues 2 to 948 of the amino acid sequence set forth in SEQ ID NO: 2;

e) a protein comprising residues 2 to 1047 of the amino acid sequence set forth in SEQ ID NO: 2; and f) a protein comprising residues 2 to 1149 of the amino acid sequence set forth in SEQ ID NO: 2.

In alternative embodiments, each of the proteins described in parts (a)-(f) of the preceding paragraph may consist of, rather than comprise, the respective amino acid sequences. Optionally, each of the proteins described in parts (a)-(f) of the preceding paragraph may further comprise methionine at their respective amino terminus. The proteins described in parts (a)-(f) of the preceding paragraph may also optionally comprise a Cys to Ser substitution at amino acid residue 26, 347, or 26 and 347 of SEQ ID NO: 1, or SEQ ID NO: 2, as appropriate. The solubility, immunogenicity, or both solubility and immunogenicity of the proteins described in parts (a)-(f) of the preceding paragraph is improved compared to proteins consisting of amino acids 2-845 of the corresponding amino acid sequence. That is, the proteins described in parts (a)-(f) of the preceding paragraph have improved solubility, improved immunogenicity, or improved solubility and improved immunogenicity compared to the LH$_N$ fragment of SEQ ID NO: 1 or SEQ ID NO: 2. In some embodiments, the proteins contain the E213Q and H216Y point mutations that abolish endopeptidase activity.

Additional examples of proteins comprising an extended LH$_N$ fragment are set forth in SEQ ID NO: 10 and SEQ ID NO: 14. Expression constructs LH$_N$/E-Hc103; LH$_N$/E-Hc202; LH$_N$/E-Hc304; and LH$_N$/E-Hc406 also contain nucleic acid sequences encoding proteins comprising an extended LH$_N$ fragment.

Proteins that comprise amino acid residues 1223 or 1224 (relative to SEQ ID NO: 1 or SEQ ID NO: 2) of neurotoxin E may further comprise an amino acid substitution at either residue 1223, residue 1224, or both residue 1223 and 1224. For example, the protein may comprise a tryptophan (W) to leucine (L) mutation at positions 1223 (i.e., W1223L), a tyrosine (Y) to phenylalanine (F) mutation at position 1224 (i.e., Y1224F), or a W1223L and a Y1224F double mutation. Examples of protein comprising these mutations are set forth in SEQ ID NO: 9 and SEQ ID NO: 13.

The invention also comprises nucleic acids encoding the various recombinant proteins described in the specification, vectors comprising those nucleic acid sequences, and methods of expressing the encoded protein in a host cell. Thus, in some embodiments, the nucleic acids encode modified *C. botulinum* or *C. butyricum* neurotoxins, such as neurotoxin E, or fragments thereof, such as an $LH_N$ fragment, that have improved solubility, immunogenicity, or both improved solubility and immunogenicity compared to the corresponding unmodified neurotoxin or neurotoxin fragment. Methods of measuring solubility and immunogenicity are known in the art, and include, but are not limited to, the methods described in the Examples.

An improvement in solubility can be accomplished by changing codons in the nucleic acid sequence that code for the amino acid cysteine to another amino acid that does not form a disulfide bond. Alternatively, or in addition, solubility can be improved by extending the sequence of a fragment, such as an $LH_N$ fragment of a clostridial neurotoxin, by providing additional sequences from an adjoining segment, such as an $H_C$ fragment of a clostridial neurotoxin.

Methods of manipulating nucleic acids and of expressing the encoded proteins are known in the art, and include those described in Molecular Cloning, A Laboratory Manual (2nd Ed., Sambrook, Fritsch and Maniatis, Cold Spring Harbor) and Current Protocols in Molecular Biology (Eds. Aufubel, Brent. Kingston, More, Feidman, Smith and Stuhl. Greene Publ. Assoc., Wiley-Interscience, NY, N.Y., 1992). Thus, it is possible to modify a nucleic acid sequence by replacing the codon for cysteine with a codon for another amino acid. In general, a cysteine is replaced with a serine, but other amino acid substitutions are also possible, such as replacement of cysteine with alanine, glycine, valine, leucine, isoleucine, or modified forms of these amino acids, so long as the replacement amino acid does not readily form disulfide bonds. Alternatively, the cysteine residue may simply be deleted from the sequence. Obviously, a deletion must remove the codon for the cysteine from the nucleic acid sequence without introducing a frameshift. Techniques for making substitution and deletion mutations at predetermined sites in a nucleic acid having a known sequence are well known and include, but are not limited to, primer mutagenesis and other forms of site-directed mutagenesis.

Similarly, methods of joining two sequence fragments, such as an $LH_N$ and an $H_C$ fragment of a clostridial neurotoxin, and of truncating a sequence, are known in the art. These include, but are not limited to, PCR-based techniques and techniques for ligating together two or more nucleic acid sequences.

Certain methods of expressing proteins are described in the Examples. Other methods can also be used, however. Generally, in order to express a protein, such as a bacterial toxin or fragment thereof, a suitable cell line is transformed with a DNA sequence encoding that protein under the control of known regulatory sequences. The transformed host cells are cultured and the protein recovered and isolated from the culture medium. The isolated expressed proteins are substantially free from other proteins with which they are co-produced as well as from other contaminants. Suitable cells or cell lines may be mammalian cells, such as Chinese hamster ovary cells (CHO), the monkey kidney COS-1 cell line, or mammalian CV-1 cells. The selection of suitable mammalian host cells and methods for transformation, culturing, amplification, screening, product production and purification are known in the art. (See, e.g., Gething and Sambrook, *Nature*, 293:620-625 (1981); Kaufman et al., *Mol Cell Biol.*, 5(7): 1750-1759 (1985); Howley et al., U.S. Pat. No. 4,419,446.))

Bacterial cells may also be used as suitable hosts for expression of a bacterial toxin or fragment thereof. For example, various strains of *E. coli* (e.g., HB101, MC1061) are well-known as host cells in the field of biotechnology. Various strains of *B. subtilis, Pseudomonas*, other bacilli and the like may also be used. For expression of a protein in bacterial cells, DNA encoding the propeptide is generally not necessary.

In some embodiments, the bacterial toxin or fragment thereof is expressed using a vector that contains a DNA sequence encoding the protein and appropriate expression control sequences. Expression control sequences for such vectors are known to those skilled in the art and may be selected depending upon the host cells. In other embodiments, the bacterial toxin or fragment thereof is expressed as a fusion protein comprising the protein sequence of the bacterial toxin or fragment thereof and, for example, a tag to stabilize the resulting fusion protein or to simplify purification of the bacterial toxin or fragment thereof. Such tags are known in the art. Representative examples include sequences which encode a series of histidine residues, the epitope tag FLAG, the Herpes simplex glycoprotein D, beta-galactosidase, maltose binding protein, streptavidin tag or glutathione S-transferase.

The invention also encompasses the methods used for improving the solubility and process characteristics of a protein. For example, in some embodiments, the disclosure provides methods for improving the solubility and process characteristics of a protein having at least one cysteine residue that forms an intermolecular disulfide bond, comprising:
(a) providing a nucleic acid sequence encoding a recombinant protein comprising at least one cysteine residue;
(b) introducing at least one point mutation into the nucleic acid sequence that substitutes at least one cysteine residue with another amino acid residue;
(c) transforming a host cell with the mutated nucleic acid sequence; and
(d) expressing the nucleic acid sequence to produce the protein.

In other embodiments, the method comprises improving the solubility of a botulinum neurotoxin, comprising:
(a) providing a nucleic acid sequence encoding a botulinum neurotoxin;
(b) modifying the nucleic acid sequence so that it encodes the $LH_N$ fragment and a portion of the $H_C$ fragment of the neurotoxin;
(c) transforming the modified nucleic acid sequence into a host cell capable of expressing the modified nucleic acid sequence; and
(d) expressing the modified nucleic acid sequence to produce the protein.

The methods for improving the solubility of a protein, such as a botulinum neurotoxin, can be entirely in vitro methods. In other embodiments, as discussed herein, the methods can include an in vivo aspect, such expressing the nucleic acid in vivo.

Unless otherwise stated, a "soluble" recombinant protein is one that is exists in solution in the cytoplasm of the host cell. If the protein contains a signal sequence the soluble protein is exported to the periplasmic space in bacteria hosts and is secreted into the culture medium in eukaryotic cells capable of secretion or by bacterial host possessing the appropriate genes. In contrast, an insoluble protein is one which exists in denatured form inside cytoplasmic granules (called an inclusion bodies) in the host cell. A soluble protein is a protein which is not found in an inclusion body inside the host cell or is found both in the cytoplasm and in inclusion bodies and in this case the protein may be present at high or low levels in the cytoplasm.

A soluble protein is distinct from a "solubilized" protein. An insoluble recombinant protein found inside an inclusion body may be solubilized (i.e., rendered into a soluble form) by treating purified inclusion bodies with denaturants such as guanidine hydrochloride, urea or sodium dodecyl sulfate (SDS). These denaturants must then be removed from the solubilized protein preparation to allow the recovered protein to renature (refold). A distinction is also made between proteins that are soluble (i.e., dissolved) in a solution devoid of significant amounts of ionic detergents (e.g., SDS) or denaturants (e.g., urea, guanidine hydrochloride) and proteins that exist as a suspension of insoluble protein molecules dispersed within the solution. A soluble protein will not be removed from a solution containing the protein by centrifugation using conditions sufficient to remove bacteria present in a liquid medium (e.g., centrifugation at 5,000 g for 4-5 minutes). A method of testing whether a protein is soluble or insoluble is described in U.S. Pat. No. 5,919,665, which is incorporated by reference.

The invention further encompasses methods of using the disclosed toxin and toxin fragments as therapeutic agents and vaccine components. Optionally, the disclosed toxin and toxin fragments are tested to ensure that they are free or substantially free of endotoxin activity. Methods of testing for endotoxin activity are known in the art.

Toxins and toxin fragments useful in vaccine compositions are those that can stimulate an antibody response that neutralizes a wild-type toxin of the same type. For example, when the toxin or toxin fragment is derived from clostridial type E neurotoxin, then the toxin or toxin fragment composition stimulates antibodies that neutralize the toxin activity of wild-type BoNT/E. By way of example only, one method for selecting clostridial neurotoxin toxins or neurotoxin fragments that can stimulate an antibody response that neutralizes wild-type BoNT activity is to determine whether the clostridial neurotoxin or neurotoxin fragment is immunoreactive with polyclonal neutralizing antibodies to wild-type BoNT of same type, such as BoNT/E. Methods of determining whether clostridial neurotoxin or neurotoxin fragment immunoreact with antibodies to wild-type BoNT include ELISA, western blot, double immunodiffusion assay, RIA, and the like. Another exemplary method comprises using the clostridial neurotoxin or neurotoxin fragments as an immunogen in mice, then determining whether the mice are protected from challenge with wild-type BoNT, such as wild-type BoNT/E.

A toxin or toxin fragment can be combined with a pharmaceutically acceptable carrier. Physiologically acceptable diluents include physiological saline solutions, and buffered saline solutions at neutral pH such as phosphate buffered saline. Other types of physiological carriers include liposomes and polymers. Optionally, the toxin or toxin fragments can be combined with an adjuvant. In some embodiments, the adjuvant is IC31 ™, produced by Intercell AG, Vienna, Austria. (See EP 1 326 634B and EP 1 296713B.) In other embodiments, the adjuvant is a Toll-like receptor (TLR) agonist, such as a TLR 4 agonist, a TLR7 agonist, or a TLR9 agonist. TLR9 agonists include, for example, immunostimulatory CpG nucleic acid sequences. Other examples of adjuvants that can be used include, but are not limited to, Freund's incomplete adjuvant, Freund's complete adjuvant, alum, monophosphoryl lipid A, alum phosphate or hydroxide, and QS-21.

For vaccine formulations, the toxins or toxin fragments can also be combined with immunomodulators, such as interleukins and interferons, for example IL-1, IL-12, and IFN-γ.

When the toxin or toxin fragment is a clostridial neurotoxin or neurotoxin fragment, multiple types of clostridial neurotoxin or neurotoxin fragments can be used together in a formulation, or a single type can be used alone. Thus, vaccine formulations and compositions include, but are not limited to, BoNT/E or a fragment of BoNT/E, such as $LH_N/E$, including $LH_N/E$ that is mutated and $LH_N/E$ that is extended by the inclusion of amino acid sequences from the $H_C$ fragments, either alone or in combination with wild-type, mutant, or fragments of one or more of clostridial neurotoxins type A, B, C, D, F, or G. Many vaccine formulations are known to those of skill in the art.

The toxin or toxin fragment is added to a vaccine formulation in an amount effective to stimulate a protective immune response in an animal challenged with wild-type toxin. Thus, in preparing a vaccine formulation, the toxin or toxin fragment is used for the manufacture of a medicament for the treatment or prevention of botulism. Generation of protective antibodies that neutralize the wild-type toxin can be measured by testing the ability of the vaccine to protect an animal, such as a mouse, from challenge with a lethal dose of wild-type toxin. The amounts of the toxin or toxin fragment in the vaccine composition that can form a protective immune response are generally about 0.1 μg to 100 mg per kg of body weight. In some cases, about 1 μg to about 1 mg/kg body weight is used. Often, about 1 μg to about 100 μg toxin or toxin fragment per kg of body weight will be sufficient to stimulate a protective immune response, such as protective antibodies. An amount of toxin or toxin fragment that stimulates a protective immune response is considered to be an "effective amount."

Depending upon the circumstances, such as the animal to be vaccinated, either a single or multiple doses of the vaccine composition are administered to provide protective immunity against the wild-type toxin. The vaccine composition can be administered to an animal in a variety of ways, including subcutaneously, intramuscularly, intravenously, intradermally, orally, intranasally, ocularly, and intraperitoneally.

Any animal that is susceptible to the wild-type toxin can be vaccinated with the toxin or toxin fragment in an immunostimulatory composition. Examples of animals susceptible to clostridial neurotoxins include, but are not limited to, rabbits, rodents, birds, horses, cattle, and humans. Accordingly, a vaccine composition comprising a clostridial neurotoxin or neurotoxin fragment, such as the clostridial neurotoxins and neurotoxin fragments described herein, can be used to protect rabbits, rodents, birds, horses, cattle, and humans, including infant humans, from botulism, or from one or more of the symptoms of botulism, such as diarrheal disease, paralysis (either mild or severe), or death.

Toxin and toxin fragments can also be used to prepare compositions comprising neutralizing antibodies that immunoreact with the wild-type toxin. The resulting antisera can be used for the manufacture of a medicament for treating exposure to clostridial neurotoxin. Thus, antibody compositions, such as the isolated antisera or antibodies purified therefrom, can be used as a passive immune serum to prevent or treat botulism in patients exposed to the wild-type toxin. In such cases, the patient is a human, including an infant, suspected of having come in contact with the toxin, or is a human, including an infant, who has had known contact with the toxin, but is not yet showing symptoms of exposure. The antibody composition can also be used in a method of treating to ameliorate symptoms in patients that are suffering from the presence of toxin in their body. When the toxin is a clostridial neurotoxin, the symptoms include diarrhea and paralysis.

Methods of preparing passive immune sera are known in the art. For example, a vaccine composition can be administered to an animal such as a horse or a human until a neutralizing antibody response to wild type toxin is generated. Neutralizing antibodies can then be harvested, purified, and administered to patients exposed to, or exhibiting symptoms of contact with, the toxin to thereby treat or prevent botulism. In some cases, the antibodies are not purified after harvesting. When the neutralizing antibodies are from humans, the antibody preparation will generally be free of viruses, such as HIV and hepatitis. Methods of preparing human antisera are known in the art, and include the methods used to prepare IVIg. The neutralizing antibodies can be administered intravenously, intramuscularly, intradermally, or subcutaneously. Antibiotic therapy can be used in conjunction. Dosages for neutralizing antibodies generally vary from about 1 mg to 1000 mg/kg. Often, they are administered at a dosage of about 50-200 mg/kg of body weight.

The invention will be further clarified by the following examples, which are intended to be purely exemplary of the invention and in no way limiting.

EXAMPLES

Example 1

Site-Directed Mutagenesis of $LH_N/E$ to Remove One or More Cysteine Residues

Endopeptidase-ablating mutations (E213Q and H216Y relative to SEQ ID NO: 1 and SEQ ID NO: 2) were introduced into the $LH_N/E$ coding sequence and the resulting cassettes cloned into plasmid vector pET26b. Various *E. coli* host strains were transformed and assessed for the ability to direct expression of a $rLH_N/E$ fragment. While high levels of target protein could be produced, recombinant $LH_N/E$ was expressed in all hosts as high molecular mass aggregate (FIGS. 1A and 1B). Those SDS-PAGE and gel filtration studies conducted under reducing and non-reducing conditions showed that $LH_N/E$ aggregation results, at least in part, from intermolecular disulfide bond formation.

It was hypothesized that aggregation could be due to the formation of cysteine-linked disulfide bonds between multiple $LH_N/E$ polypeptides. Molecular biology approaches were pursued to increase expression of soluble, non-aggregated $rLH_N/E$ protein. Using computational analyses of the BoNT/E catalytic domain crystal structure two surface-proximal cysteine residues (Cys26 and Cys347 in SEQ ID NO: 1 and SEQ ID NO: 2) have been identified that most likely participate in intermolecular disulfide-bond-mediated bridging. Those residues were targeted for mutagenesis, and the aggregation properties of the mutated proteins were assessed.

$LH_N/E$ was cloned into the expression vector pET26b (Novagen) and this plasmid clone was used for the mutagenesis procedure. Specifically, site directed mutagenesis (QuikChange II XL site-directed mutagenesis kit, Stratagene) was used to introduce two point mutations into the $LH_N/E$ gene that change codons 26 and 347 (relative to a nucleic acid sequence encoding SEQ ID NO: 1 or SEQ ID NO: 2) from cysteine to structurally similar serine. While it is preferable to substitute the cysteine residue with a structurally similar amino acid, any amino acid may be substituted as long as that amino acid is incapable of forming an intermolecular disulfide bond.

The primer names and sequences used for mutagenesis are shown, with the nucleotides responsible for the cysteine to serine changes underlined. For both mutations, a TGC codon (cysteine) was changed to an AGC codon (serine). These two primers were used for the C26S mutation: C26S-LhnEfor: 5'-GTATATTAAACCGGGCGGC AGCCAGGAGTTTTATAAA AGC-3' (SEQ ID NO: 3) and C26S-LhnErev: 5'-GCTTTTATAAAACTCCTGG C TGCCGCCCGGTTTAATATAC-3' (SEQ ID NO: 4). These two primers were used for the C347S mutation: C347S-LhnEfor: 5'-GTACCAAATTTCAGGTGA AG AGCCGCCAAACCTACATCG-3' (SEQ ID NO: 5) and C347S-LhnErev: 5'-CGATGTAGGTTTGGCGGC TCTTCACCTGAAATTTGGTAC-3' (SEQ ID NO: 6).

Clones of pET26b/$LH_N/E$ containing each single point mutation and both point mutations were made. The C26S single mutant, C347S single mutant, and C26S/C347S double mutant clones were expressed and analyzed for disulfide bond-mediated aggregation. As shown in FIGS. 2A and 2B, analysis of reduced and non-reduced samples revealed that intermolecular disulfide bonding was abolished in each of the $LH_N/E$ clones (C26S single mutant, C347S single mutant, and C26S, C347S double mutant), whereas intermolecular disulfide bond formation was observable for the parental $LH_N/E$ clone lacking the serine substitutions.

Example 2

Extending the $LH_N/E$ Fragment with $H_C$ Sequence Improves Solubility

The solubility of clostridial neurotoxin proteins can also be enhanced by creating proteins in which an $LH_N$ domain, or a fragment of an $LH_N$ domain, is expressed along with amino acid sequence from an Hc domain.

Recombinant truncated forms of the botulinum serotype E toxin, such as the $LH_N$ fragments, have proven difficult to produce (express) and purify due to low solubility. Even at low concentrations, insoluble forms are often expressed in a non-native multimeric and aggregated state which renders them poor immunogens and unable to elicit protective levels of toxin neutralizing antibodies. To address this issue and enable the production of soluble (and possibly monomeric) protein, recombinant derivatives of the $LH_N/E$ protein have been produced that carry various lengths of the adjoining Hc domain.

The following expression constructs were tested for protein solubility in the *E. coli* strain ER2566: $LH_N/E$; $LH_N/E$-Hc103; $LH_N/E$-Hc202; $LH_N/E$-Hc304; and $LH_N/E$-Hc406. Fifteen milliliters of LB media containing kanamycin (30 μg/mL) were inoculated with each strain containing the construct listed above. Inoculations were made directly from frozen glycerol stocks. These cultures grew at 37° C. overnight with shaking. The next morning, the overnight cultures were diluted into 1 L of 2×YT containing kanamycin (30 μg/mL) (15 mL into 1 L of 2×YT) in Fernbach flasks. The cultures shook at 37° C. for three hours. $OD_{600}$ ranged from 0.7-0.9 for all of the cultures. The Fernbach flasks were moved into 20° C. incubators, IPTG was added to 1 mM final concentration, and the flasks shook at 20° C. for 4 hours.

The 1 L cultures were collected by centrifugation and cell pellets were resuspended in 200 ml of 50 mM Tris, pH 8.0, 25 mM EDTA, pH 8.0. The cell suspensions were disrupted using the microfluidizer. Thirty-five milliliters of each cell lysate was centrifuged at 10,000×g for 30 minutes. The supernatants containing soluble protein were transferred into clean tubes and the insoluble pellets were resuspended in 35 mL of 50 mM Tris, pH 8.0, 25 mM EDTA, pH 8.0.

Equal volumes of total cell lysate, and soluble and insoluble fractions, were prepared for SDS-PAGE by the addition of sample buffer and boiling for 5 minutes. Equal amounts of each sample were subjected to SDS-PAGE. One set of gels was stained using MicroWave Blue reagent. Another set was transferred to PVDF membrane and subjected to western blotting using antisera specific for BoNT/E obtained from the Health Protection Agency.

Figure 3A:
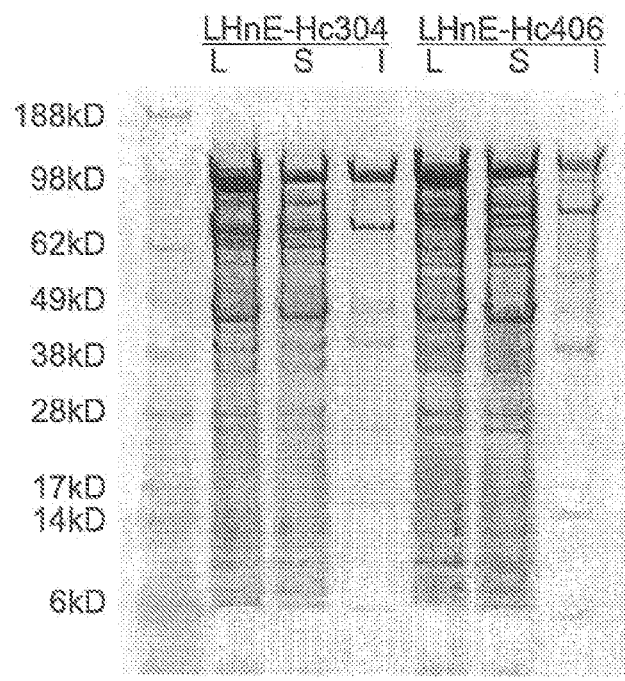
FIGS. 3A and 3B are Coomassie Blue stained gels demonstrating that the solubility of the $LH_N/E$-Hc protein increases as the length of the Hc sequence included in the protein increases.
Figure 3B:
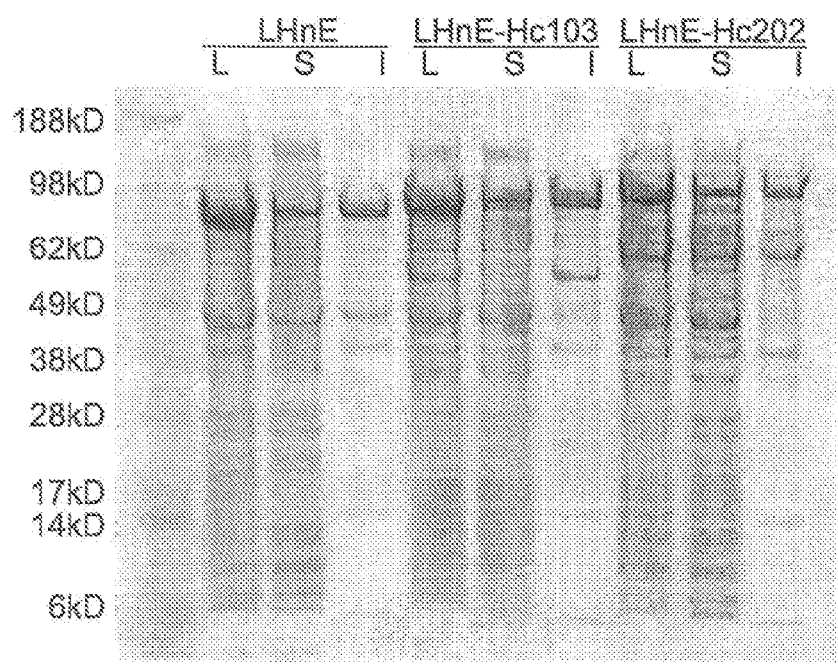
Figure 4A:
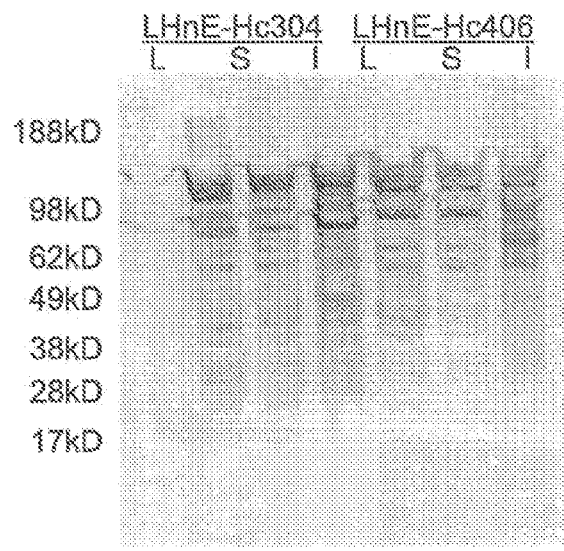
FIGS. 4A and 4B are western blots demonstrating that the solubility of the LH$_N$/E-Hc protein increases as the length of the Hc sequence included in the protein increases.
Figure 4B:
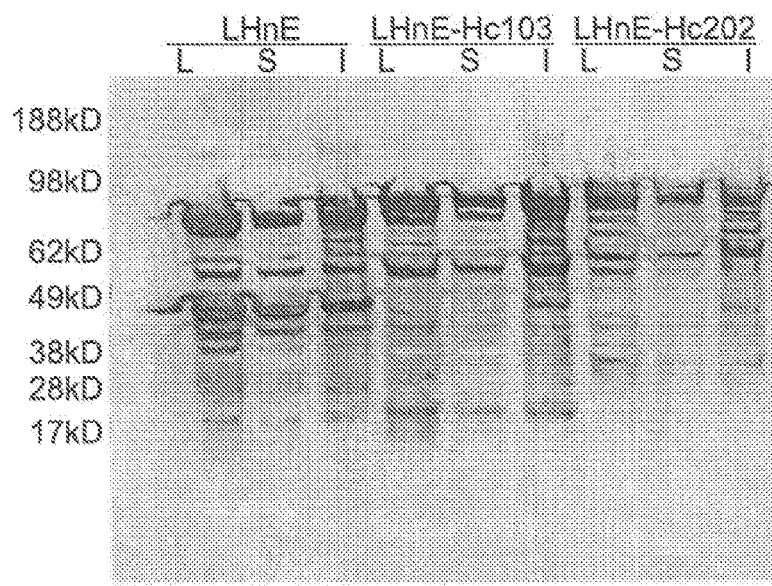

The $LH_N/E$ solubility is enhanced with the addition of amino acid residues from the Hc domain. This can be seen by comparing the amount of $LH_N/E$-Hc in soluble versus insoluble fractions in the Coomassie stained gels of FIG. 3 and the western blots of FIG. 4. $LH_N/E$, which is devoid of any Hc sequence, is detected predominately in the insoluble fraction. This is also observed for $LH_N/E$-Hc103 and $LH_N/E$-Hc202. However, the solubility of recombinant proteins containing longer segments of the Hc domains is greatly enhanced. This can be seen for $LH_N/E$-Hc406, which fractionates predominately with the soluble fraction, and also with $LH_N/E$-Hc304, which also displays enhanced solubility. These conclusions were confirmed by densitometry scans of the Coomassie stained gel.

Figure 5A:
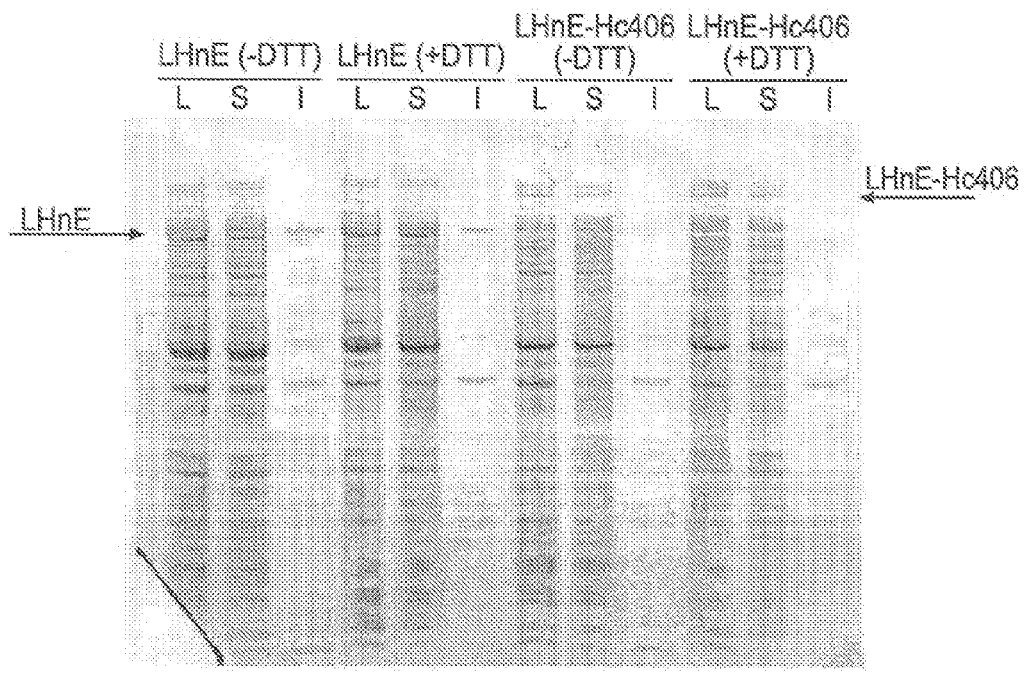
FIGS. 5A and 5B are a Coomassie Blue stained gel and western blot analysis, respectively, of the solubility of the LH$_N$/E and LH$_N$/E-H$_C$406 proteins in the presence of the reducing agent DTT.
Figure 5B:
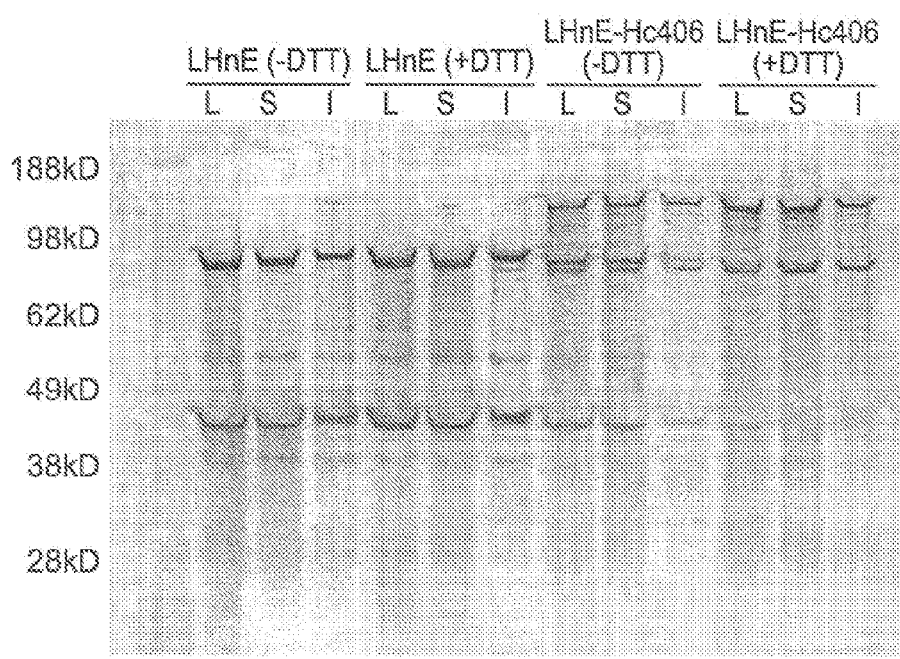

We also compared the effect of treating $LH_N/E$ and $LH_N/E$-Hc406 with the reducing agent DTT. FIG. 5A shows a Coomassie stained gel and FIG. 5B a western blot of the DTT treated (+DTT) and untreated (−DTT) samples. In both the presence and absence of DTT, more $LH_N/E$-Hc406 was found in the soluble (S) than in the insoluble (I) fraction.

Figure 6:
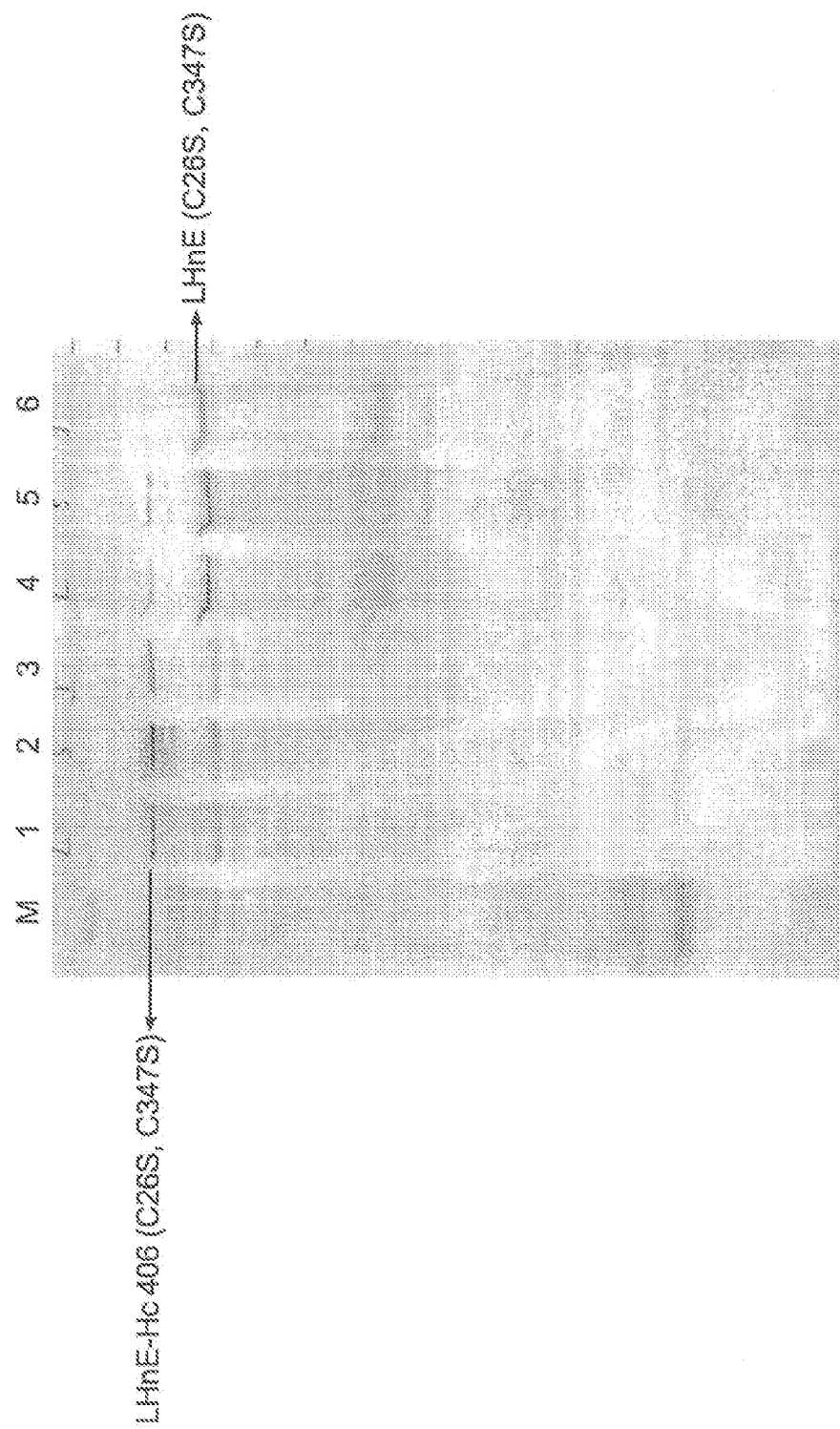
FIG. 6 is a western blot comparing protein levels in total lysate, the soluble fraction, and the insoluble fraction for LH$_N$ proteins comprising Cys to Ser replacements at positions 26 and 347, and having or lacking an Hc fragment.

The addition of $H_C$ sequence to the $LH_N/E$ fragment improves its solubility, as does the replacement of Cys 26 and Cys 347 with serine residues. We have also prepared expression constructs in which we combined these approaches. Following induction of protein expression, the pellet was harvested, then lysed and microfluidized. The lysate was separated into soluble and insoluble fractions by centrifugation. The levels of protein in the total lysate, soluble fraction, and insoluble fraction compared by running on a gel and western blotting with the anti-BoNT/E antisera. As shown in FIG. 6, the $LH_N/E$-Hc406 (C26S, C347S) mutant, like the $LH_N/E$ (C26S, C347S) mutant, partitions predominantly to the soluble fraction.

Example 3

Immunogenicity of $LH_N/E$ Cys to Ser Fragments and $LH_N/E$-Hc Fragments

Abolishing the ability of $LH_N/E$ to form aberrant intermolecular disulfide bonds by replacing cysteine residues with amino acids that do not form disulfide bonds and extending the $LH_N/E$ fragment with $H_C$ sequence are two techniques that improve the yield of monomeric or less aggregated protein. These modifications will enhance the immunogenicity and protective efficacy of the $LH_N/E$ fragment and the enzymatic activity of non-endopeptidase ablated toxins and toxin subfragments.

Immunogenicity of the recombinant proteins is tested in mice. Mice are immunized either with 10 μg of a $LH_N/E$ protein in which one or more cysteine residues has been replaced with another amino acid that does not form disulfide bonds, with 10 μg of a $LH_N/E$ protein that has been extended by inclusion of $H_C$ sequence, with 10 μg of inactivated BoNT/E, or with other proteins described in the Examples. The proteins are suspended in an adjuvant emulsion. Control mice are immunized with saline emulsified in adjuvant for use as negative controls. The mice are immunized i.p. four times at 2-week intervals. One week after the last immunization, the mice are bled and the serum is analyzed by immunoblot for the presence of specific antibody. ELISA is used to determine the titer of the antisera. Two weeks after the last immunization, each mouse is challenged i.p. with 2 lethal doses of BoNT/E. Four days after challenge, the mice are scored for survivors.

Example 4

Amino Acid Sequences Encoded by Certain Constructs

The following amino acid sequences are encoded by constructs in which the type E neurotoxin is from *Clostridium botulinum*. In the sequences, the mutated cysteine residues, which have been substituted with serine residues, are indicated in bold and underline.

```
1. LH_N/E (endopeptidase active):
                                                    (SEQ ID NO: 7)
PKINSFNYNDPVNDRTILYIKPGGSQEFYKSFNIMKNIWIIPERNVIGTTPQDFHPP

TSLKNGDSSYYDPNYLQSDEEKDRFLKIVTKIFNRINNNLSGGILLEELSKANPYLG

NDNTPDNQFHIGDASAVEIKFSNGSQDILLPNVIIMGAEPDLFETNSSNISLRNNYM

PSNHRFGSIAIVTFSPEYSFRFNDNCMNEFIQDPALTLMHELIHSLHGLYGAKGITT

KYTITQKQNPLITNIRGTNIEEFLTFGGTDLNIITSAQSNDIYTNLLADYKKIASKL

SKVQVSNPLLNPYKDVFEAKYGLDKDASGIYSVNINKFNDIFKKLYSFTEFDLRTKF

QVKSRQTYIGQYKYFKLSNLLNDSIYNISEGYNINNLKVNFRGQNANLNPRIITPIT

GRGLVKKIIRFCKNIVSVKGIRKSICIEINNGELFFVASENSYNDDNINTPKEIDDT

VTSNNNYENDLDQVILNFNSESAPGLSDEKLNLTIQNDAYIPKYDSNGTSDIEQHDV

NELNVFFYLDAQKVPEGENNVNLTSSIDTALLEQPKIYTFFSSEFINNVNKPVQAAL
```

FVSWIQQVLVDFTTEANQKSTVDKIADISIVVPYIGLALNIGNEAQKGNFKDALELL

GAGILLEFEPELLIPTILVFTIKSFLGSSDNKNKVIKAINNALKERDEKWKEVYSFI

VSNWMTKINTQFNKRKEQMYQALQNQVNAIKTIIESKYNSYTLEEKNELTNKYDIKQ

IENELNQKVSIAMNNIDRFLTESSISYLMKIINEVKINKLREYDENVKTYLLNYIIQ

HGSILGESQQELNSMVTDTLNNSIPFKLSSYTDDKILISYFNKFFK.

2. LH$_N$/E (endopeptidase attenuated):

(SEQ ID NO: 8)

PKINSFNYNDPVNDRTILYIKPGGSQEFYKSFNIMKNIWIIPERNVIGTTPQDFHPP

TSLKNGDSSYYDPNYLQSDEEKDRFLKIVTKIFNRINNNLSGGILLEELSKANPYLG

NDNTPDNQFHIGDASAVEIKFSNGSQDILLPNVIIMGAEPDLFETNSSNISLRNNYM

PSNHRFGSIAIVTFSPEYSFRFNDNCMNEFIQDPALTLMHQLIYSLHGLYGAKGITT

KYTITQKQNPLITNIRGTNIEEFLTFGGTDLNIITSAQSNDIYTNLLADYKKIASKL

SKVQVSNPLLNPYKDVFEAKYGLDKDASGIYSVNINKFNDIFKKLYSFTEFDLRTKF

QVKSRQTYIGQYKYFKLSNLLNDSIYNISEGYNINNLKVNFRGQNANLNPRIITPIT

GRGLVKKIIRFCKNIVSVKGIRKSICIEINNGELFFVASENSYNDDNINTPKEIDDT

VTSNNNYENDLDQVILNFNSESAPGLSDEKLNLTIQNDAYIPKYDSNGTSDIEQHDV

NELNVFFYLDAQKVPEGENNVNLTSSIDTALLEQPKIYTFFSSEFINNVNKPVQAAL

FVSWIQQVLVDFTTEANQKSTVDKIADISIVVPYIGLALNIGNEAQKGNFKDALELL

GAGILLEFEPELLIPTILVFTIKSFLGSSDNKNKVIKAINNALKERDEKWKEVYSFI

VSNWMTKINTQFNKRKEQMYQALQNQVNAIKTIIESKYNSYTLEEKNELTNKYDIKQ

IENELNQKVSIAMNNIDRFLTESSISYLMKIINEVKINKLREYDENVKTYLLNYIIQ

HGSILGESQQELNSMVTDTLNNSIPFKLSSYTDDKILISYFNKFFK.

3. BoNT/E neurotoxin (endopeptidase attenuated):

(SEQ ID NO: 9)

PKINSFNYNDPVNDRTILYIKPGGSQEFYKSFNIMKNIWIIPERNVIGTTPQDFHPP

TSLKNGDSSYYDPNYLQSDEEKDRFLKIVTKIFNRINNNLSGGILLEELSKANPYLG

NDNTPDNQFHIGDASAVEIKFSNGSQDILLPNVIIMGAEPDLFETNSSNISLRNNYM

PSNHRFGSIAIVTFSPEYSFRFNDNCMNEFIQDPALTLMHQLIYSLHGLYGAKGITT

KYTITQKQNPLITNIRGTNIEEFLTFGGTDLNIITSAQSNDIYTNLLADYKKIASKL

SKVQVSNPLLNPYKDVFEAKYGLDKDASGIYSVNINKFNDIFKKLYSFTEFDLRTKF

QVKSRQTYIGQYKYFKLSNLLNDSIYNISEGYNINNLKVNFRGQNANLNPRIITPIT

GRGEVKKIIRFCKNIVSVKGIRKSICIEINNGELFFVASENSYNDDNINTPKEIDDT

VTSNNNYENDLDQVILNFNSESAPGLSDEKLNLTIQNDAYIPKYDSNGTSDIEQHDV

NELNVFFYLDAQKVPEGENNVNLTSSIDTALLEQPKIYTFFSSEFINNVNKPVQAAL

FVSWIQQVLVDFTTEANQKSTVDKIADISIVVPYIGLALNIGNEAQKGNFKDALELL

GAGILLEFEPELLIPTILVFTIKSFLGSSDNKNKVIKAINNALKERDEKWKEVYSFI

VSNWMTKINTQFNKRKEQMYQALQNQVNAIKTIIESKYNSYTLEEKNELTNKYDIKQ

IENELNQKVSIAMNNIDRFLTESSISYLMKIINEVKINKLREYDENVKTYLLNYIIQ

HGSILGESQQELNSMVTDTLNNSIPFKLSSYTDDKILISYFNKFFKRIKSSSVLNMR

YKNDKYVDTSGYDSNININGDVYKYPTNKNQFGIYNDKLSEVNISQNDYIIYDNKYK

NFSISFWVRIPNYDNKIVNVNNEYTIINCMRDNNSGWKVSLNHNEIIWTFEDNRGIN

QKLAFNYGNANGISDYINKWIFVTITNDRLGDSKLYINGNLIDQKSILNLGNIHVSD

-continued

NILFKIVNCSYTRYIGIRYFNIFDKELDETEIQTLYSNEPNTNILKDFWGNYLLYDK

EYYLLNVLKPNNFIDRRKDSTLSINNIRSTILLANRLYSGIKVKIQRVNNSSTNDNL

VRKNDQVYINFVASKTHLFPLYADTATTNKEKTIKISSSGNRFNQVVVMNSVGNCTM

NFKNNNGNNIGLLGFKADTVVASTLFYTHMRDHTNSNGCFWNFISEEHGWQEK.

4. Extended LH$_N$/E neurotoxin (endopeptidase attenuated):

(SEQ ID NO: 10)

PKINSFNYNDPVNDRTILYIKPGGSQEFYKSFNIMKNIWIIPERNVIGTTPQDFHPP

TSLKNGDSSYYDPNYLQSDEEKDRFLKIVTKIFNRINNNLSGGILLEELSKANPYLG

NDNTPDNQFHIGDASAVEIKFSNGSQDILLPNVIIMGAEPDLFETNSSNISLRNNYM

PSNHRFGSIAIVTFSPEYSFRFNDNCMNEFIQDPALTLMHQLIYSLHGLYGAKGITT

KYTITQKQNPLITNIRGTNIEEFLTFGGTDLNIITSAQSNDIYTNLLADYKKIASKL

SKVQVSNPLLNPYKDVFEAKYGLDKDASGIYSVNINKFNDIFKKLYSFTEFDLRTKF

QVKSRQTYIGQYKYFKLSNLLNDSIYNISEGYNINNLKVNFRGQNANLNPRIITPIT

GRGLVKKIIRFCKNIVSVKGIRKSICIEINNGELFFVASENSYNDDNINTPKEIDDT

VTSNNNYENDLDQVILNFNSESAPGLSDEKLNLTIQNDAYIPKYDSNGTSDIEQHDV

NELNVFFYLDAQKVPEGENNVNLTSSIDTALLEQPKIYTFFSSEFINNVNKPVQAAL

FVSWIQQVLVDFTTEANQKSTVDKIADISIVVPYIGLALNIGNEAQKGNFKDALELL

GAGILLEFEPELLIPTILVFTIKSFLGSSDNKNKVIKAINNALKERDEKWKEVYSFI

VSNWMTKINTQFNKRKEQMYQALQNQVNAIKTIIESKYNSYTLEEKNELTNKYDIKQ

IENELNQKVSIAMNNIDRFLTESSISYLMKIINEVKINKLREYDENVKTYLLNYIIQ

HGSILGESQQELNSMVTDTLNNSIPFKLSSYTDDKILISYFNKFFKRIKSSSVLNMR

YKNDKYVDTSGYDSNININGDVYKYPTNKNQFGIYNDKLSEVNISQNDYIIYDNKYK

NFSISFWVRIPNYDNKIVNVNNEYTIINCMRDNNSGWKVSLNHNEIIWTFEDNRGIN

QKLAFNYGNANGISDYINKWIFVTITNDRLGDSKLYINGNLIDQKSILNLGNIHVSD

NILFKIVNCSYTRYIGIRYFNIFDKELDETEIQTLYSNE.

40

The following amino acid sequences are encoded by constructs in which the type E neurotoxin is from *Clostridium butyricum*. In the sequences, the mutated cysteine residues, which have been substituted with serine residues, are indicated in bold and underline.

5. LH$_N$/E (endopeptidase active):

(SEQ ID NO: 11)

PTINSFNYNDPVNNRTILYIKPGGSQQFYKSFNIMKNIWIIPERNVIGTIPQDFLPP

TSLKNGDSSYYDPNYLQSDQEKDKFLKIVTKIFNRINDNLSGRILLEELSKANPYLG

NDNTPDGDFIINDASAVPIQFSNGSQSILLPNVIIMGAEPDLFETNSSNISLRNNYM

PSNHGFGSIAIVTFSPEYSFRFKDNSMNEFIQDPALTLMHELIHSLHGLYGAKGITT

KYTITQKQNPLITNIRGTNIEEFLTFGGTDLNIITSAQSNDIYTNLLADYKKIASKL

SKVQVSNPLLNPYKDVFEAKYGLDKDASGIYSVNINKFNDIFKKLYSFTEFDLATKF

QVKSRQTYIGQYKYFKLSNLLNDSIYNISEGYNINNLKVNFRGQNANLNPRIITPIT

GRGLVKKIIRFCKNIVSVKGIRKSICIEINNGELFFVASENSYNDDNINTPKEIDDT

VTSNNNYENDLDQVILNFNSESAPGLSDEKLNLTIQNDAYIPKYDSNGTSDIEQHDV

NELNVFFYLDAQKVPEGENNVNLTSSIDTALLEQPKIYTFFSSEFINNVNKPVQAAL

FVGWIQQVLVDFTTEANQKSTVDKIADISIVVPYIGLALNIGNEAQKGNFKDALELL

-continued

GAGILLEFEPELLIPTILVFTIKSFLGSSDNKNKVIKAINNALKERDEKWKEVYSFI

VSNWMTKINTQFNKRKEQMYQALQNQVNALKAIIESKYNSYTLEEKNELTNKYDIEQ

IENELNQKVSIAMNNIDRFLTESSISYLMKLINEVKINKLREYDENVKTYLLDYIIK

HGSILGESQQELNSMVIDTLNNSIPFKLSSYTDDKILISYFNKFFK.

6. LH$_N$/E (endopeptidase attenuated):

(SEQ ID NO: 12)

PTINSFNYNDPVNNRTILYIKPGGSQQFYKSFNIMKNIWIIPERNVIGTIPQDFLPP

TSLKNGDSSYYDPNYLQSDQEKDKFLKIVTKIFNRINDNLSGRILLEELSKANPYLG

NDNTPDGDFIINDASAVPIQFSNGSQSILLPNVIIMGAEPDLFETNSSNISLRNNYM

PSNHGFGSIAIVTFSPEYSFRFKDNSMNEFIQDPALTLMHQLIYSLHGLYGAKGITT

KYTITQKQNPLITNIRGTNIEEFLTFGGTDLNIITSAQSNDIYTNLLADYKKIASKL

SKVQVSNPLLNPYKDVFEAKYGLDKDASGIYSVNINKFNDIFKKLYSFTEFDLATKF

QVKSRQTYIGQYKYFKLSNLLNDSIYNISEGYNINNLKVNFRGQNANLNPRIITPIT

GRGLVKKIIRFCKNIVSVKGIRKSICIEINNGELFFVASENSYNDDNINTPKEIDDT

VTSNNNYENDLDQVILNFNSESAPGLSDEKLNLTIQNDAYIPKYDSNGTSDIEQHDV

NELNVFFYLDAQKVPEGENNVNLTSSIDTALLEQPKIYTFFSSEFINNVNKPVQAAL

FVGWIQQVLVDFTTEANQKSTVDKIADISIVVPYIGLALNIGNEAQKGNFKDALELL

GAGILLEFEPELLIPTILVFTIKSFLGSSDNKNKVIKAINNALKERDEKWKEVYSFI

VSNWMTKINTQFNKRKEQMYQALQNQVNALKAIIESKYNSYTLEEKNELTNKYDIEQ

IENELNQKVSIAMNNIDRFLTESSISYLMKLINEVKINKLREYDENVKTYLLDYIIK

HGSILGESQQELNSMVIDTLNNSIPFKLSSYTDDKILISYFNKFFK.

7. BoNT/E neurotoxin (endopeptidase attenuated):

(SEQ ID NO: 13)

PTINSFNYNDPVNNRTILYIKPGGSQQFYKSFNIMKNIWIIPERNVIGTIPQDFLPP

TSLKNGDSSYYDPNYLQSDQEKDKFLKIVTKIFNRINDNLSGRILLEELSKANPYLG

NDNTPDGDFIINDASAVPIQFSNGSQSILLPNVIIMGAEPDLFETNSSNISLRNNYM

PSNHGFGSIAIVTFSPEYSFRFKDNSMNEFIQDPALTLMHQLIYSLHGLYGAKGITT

KYTITQKQNPLITNIRGTNIEEFLTFGGTDLNIITSAQSNDIYTNLLADYKKIASKL

SKVQVSNPLLNPYKDVFEAKYGLDKDASGIYSVNINKFNDIFKKLYSFTEFDLATKF

QVKSRQTYIGQYKYFKLSNLLNDSIYNISEGYNINNLKVNFRGQNANLNPRIITPIT

GRGLVKKIIRFCKNIVSVKGIRKSICIEINNGELFFVASENSYNDDNINTPKEIDDT

VTSNNNYENDLDQVILNFNSESAPGLSDEKLNLTIQNDAYIPKYDSNGTSDIEQHDV

NELNVFFYLDAQKVPEGENNVNLTSSIDTALLEQPKIYTFFSSEFINNVNKPVQAAL

FVGWIQQVLVDFTTEANQKSTVDKIADISIVVPYIGLALNIGNEAQKGNFKDALELL

GAGILLEFEPELLIPTILVFTIKSFLGSSDNKNKVIKAINNALKERDEKWKEVYSFI

VSNWMTKINTQFNKRKEQMYQALQNQVNALKAIIESKYNSYTLEEKNELTNKYDIEQ

IENELNQKVSIAMNNIDRFLTESSISYLMKLINEVKINKLREYDENVKTYLLDYIIK

HGSILGESQQELNSMVIDTLNNSIPFKLSSYTDDKILISYFNKFFKRIKSSSVLNMR

YKNDKYVDTSGYDSNININGDVYKYPTNKNQFGIYNDKLSEVNISQNDYIIYDNKYK

NFSISFWVRIPNYDNKIVNVNNEYTIINCMRDNNSGWKVSLNHNEIIWTLQDNSGIN

QKLAFNYGNANGISDYINKWIFVTITNDRLGDSKLYINGNLIDKKSILNLGNIHVSD

NILFKIVNCSYTRYIGIRYFNIFDKELDETEIQTLYNNEPNANILKDFWGNYLLYDK

EYYLLNVLKPNNFINRRTDSTLSINNIRSTILLANRLYSGIKVKIQRVNNSSTNDNL

-continued

```
VRKNDQVYINFVASKTHLLPLYADTATTNKEKTIKISSSGNRFNQVVVMNSVGNCTM

NFKNNNGNNIGLLGFKADTVVASTLFYTHMRDNTNSNGFFWNFISEEHGWQEK.

8. Extended LH_N/E (endopeptidase attenuated):
                                                  (SEQ ID NO: 14)
PKINSFNYNDPVNDRTILYIKPGGSQEFYKSFNIMKNIWIIPERNVIGTTPQDFHPP

TSLKNGDSSYYDPNYLQSDEEKDRFLKIVTKIFNRINNNLSGGILLEELSKANPYLG

NDNTPDNQFHIGDASAVEIKFSNGSQDILLPNVIIMGAEPDLFETNSSNISLRNNYM

PSNHRFGSIAIVTFSPEYSFRFNDNCMNEFIQDPALTLMHQLIYSLHGLYGAKGITT

KYTITQKQNPLITNIRGTNIEEFLTFGGTDLNIITSAQSNDIYTNLLADYKKIASKL

SKVQVSNPLLNPYKDVFEAKYGLDKDASGIYSVNINKFNDIFKKLYSFTEFDLRTKF

QVKSRQTYIGQYKYFKLSNLLNDSIYNISEGYNINNLKVNFRGQNANLNPRIITPIT

GRGLVKKIIRFCKNIVSVKGIRKSICIEINNGELFFVASENSYNDDNINTPKEIDDT

VTSNNNYENDLDQVILNFNSESAPGLSDEKLNLTIQNDAYIPKYDSNGTSDIEQHDV

NELNVFFYLDAQKVPEGENNVNLTSSIDTALLEQPKIYTFFSSEFINNVNKPVQAAL

FVSWIQQVLVDFTTEANQKSTVDKIADISIVVPYIGLALNIGNEAQKGNFKDALELL

GAGILLEFEPELLIPTILVFTIKSFLGSSDNKNKVIKAINNALKERDEKWKEVYSFI

VSNWMTKINTQFNKRKEQMYQALQNQVNAIKTIIESKYNSYTLEEKNELTNKYDIKQ

IENELNQKVSIAMNNIDRFLTESSISYLMKIINEVKINKLREYDENVKTYLLNYIIQ

HGSILGESQQELNSMVTDTLNNSIPFKLSSYTDDKILISYFNKFFKRIKSSSVLNMR

YKNDKYVDTSGYDSNININGDVYKYPTNKNQFGIYNDKLSEVNISQNDYIIYDNKYK

NFSISFWVRIPNYDNKIVNVNNEYTIINCMRDNNSGWKVSLNHNEIIWTFEDNRGIN

QKLAFNYGNANGISDYINKWIFVTITNDRLGDSKLYINGNLIDQKSILNLGNIHVSD

NILFKIVNCSYTRYIGIRYFNIFDKELDETEIQTLYSNE.
```

Other embodiments of the invention will be apparent to those skilled in the art from consideration of the specification and practice of the invention disclosed herein, such as, for example, *C. botulinum* neurotoxins of type A, B, C, D, F, or G mutated or truncated according to the method of the invention that exhibit improved solubility. It is intended that the specification and examples be considered as exemplary only, with the true scope and spirit of the invention being indicated by the following claims.

---

What is claimed is:

1. A method of making a recombinant protein comprising:
   (a) transforming an *E. coli* host cell with a nucleic acid sequence encoding a protein comprising the $LH_N$ fragment of *Clostridium botulinum* or *Clostridium butyricum* neurotoxin E having at least one point mutation that substitutes a cysteine residue with another amino acid residue; and
   (b) expressing the nucleic acid sequence to produce the recombinant protein.

2. The method of claim 1, wherein the amino acid introduced by the at least one point mutation is a serine.

3. The method of claim 1, wherein the protein comprises the $LH_N$ fragment of SEQ ID NO: 1 or SEQ ID NO: 2 having a substitution of serine for cysteine at amino acid residue 26, amino acid residue 347, or both amino acid residue 26 and amino acid residue 347.

4. The method of claim 1, further comprising isolating the protein.

5. The method of claim 1, wherein the protein has active endopeptidase activity.

6. The method of claim 1, wherein the protein has attenuated endopeptidase activity.

7. The method of claim 1, wherein the protein comprises the $LH_N$ fragment of SEQ ID NO: 1 having a substitution of serine for cysteine at amino acid residue 198.

8. The method of claim 1, wherein the protein comprises at least a portion of the $H_C$ fragment of the neurotoxin.

9. The method of claim 8, wherein the protein comprises the $H_C$ fragment of the neurotoxin.

10. The method of claim 2, wherein the protein comprises the $LH_N$ fragment of SEQ ID NO: 1 having a substitution of serine for cysteine at amino acid residue 198.

11. The method of claim 2, wherein the protein comprises at least a portion of the $H_C$ fragment of the neurotoxin.

12. The method of claim 11, wherein the protein comprises the $H_C$ fragment of the neurotoxin.

* * * * *

SEQUENCE LISTING

<160> NUMBER OF SEQ ID NOS: 14

<210> SEQ ID NO 1
<211> LENGTH: 1251
<212> TYPE: PRT
<213> ORGANISM: Clostridium botulinum

<400> SEQUENCE: 1

```
Met Pro Lys Ile Asn Ser Phe Asn Tyr Asn Asp Pro Val Asn Asp Arg
 1               5                  10                  15

Thr Ile Leu Tyr Ile Lys Pro Gly Gly Cys Gln Glu Phe Tyr Lys Ser
             20                  25                  30

Phe Asn Ile Met Lys Asn Ile Trp Ile Ile Pro Glu Arg Asn Val Ile
         35                  40                  45

Gly Thr Thr Pro Gln Asp Phe His Pro Pro Thr Ser Leu Lys Asn Gly
```

```
                 50                      55                      60
Asp Ser Ser Tyr Tyr Asp Pro Asn Tyr Leu Gln Ser Asp Glu Glu Lys
 65                      70                      75                      80
Asp Arg Phe Leu Lys Ile Val Thr Lys Ile Phe Asn Arg Ile Asn Asn
                 85                      90                      95
Asn Leu Ser Gly Gly Ile Leu Leu Glu Glu Leu Ser Lys Ala Asn Pro
                100                     105                     110
Tyr Leu Gly Asn Asp Asn Thr Pro Asp Asn Gln Phe His Ile Gly Asp
                115                     120                     125
Ala Ser Ala Val Glu Ile Lys Phe Ser Asn Gly Ser Gln Asp Ile Leu
        130                     135                     140
Leu Pro Asn Val Ile Ile Met Gly Ala Glu Pro Asp Leu Phe Glu Thr
145                     150                     155                     160
Asn Ser Ser Asn Ile Ser Leu Arg Asn Asn Tyr Met Pro Ser Asn His
                165                     170                     175
Arg Phe Gly Ser Ile Ala Ile Val Thr Phe Ser Pro Glu Tyr Ser Phe
                180                     185                     190
Arg Phe Asn Asp Asn Cys Met Asn Glu Phe Ile Gln Asp Pro Ala Leu
                195                     200                     205
Thr Leu Met His Glu Leu Ile His Ser Leu His Gly Leu Tyr Gly Ala
210                     215                     220
Lys Gly Ile Thr Thr Lys Tyr Thr Ile Thr Gln Lys Gln Asn Pro Leu
225                     230                     235                     240
Ile Thr Asn Ile Arg Gly Thr Asn Ile Glu Glu Phe Leu Thr Phe Gly
                245                     250                     255
Gly Thr Asp Leu Asn Ile Ile Thr Ser Ala Gln Ser Asn Asp Ile Tyr
                260                     265                     270
Thr Asn Leu Leu Ala Asp Tyr Lys Lys Ile Ala Ser Lys Leu Ser Lys
        275                     280                     285
Val Gln Val Ser Asn Pro Leu Leu Asn Pro Tyr Lys Asp Val Phe Glu
        290                     295                     300
Ala Lys Tyr Gly Leu Asp Lys Asp Ala Ser Gly Ile Tyr Ser Val Asn
305                     310                     315                     320
Ile Asn Lys Phe Asn Asp Ile Phe Lys Lys Leu Tyr Ser Phe Thr Glu
                325                     330                     335
Phe Asp Leu Arg Thr Lys Phe Gln Val Lys Cys Arg Gln Thr Tyr Ile
                340                     345                     350
Gly Gln Tyr Lys Tyr Phe Lys Leu Ser Asn Leu Leu Asn Asp Ser Ile
        355                     360                     365
Tyr Asn Ile Ser Glu Gly Tyr Asn Ile Asn Asn Leu Lys Val Asn Phe
        370                     375                     380
Arg Gly Gln Asn Ala Asn Leu Asn Pro Arg Ile Ile Thr Pro Ile Thr
385                     390                     395                     400
Gly Arg Gly Leu Val Lys Lys Ile Ile Arg Phe Cys Lys Asn Ile Val
                405                     410                     415
Ser Val Lys Gly Ile Arg Lys Ser Ile Cys Ile Glu Ile Asn Asn Gly
                420                     425                     430
Glu Leu Phe Phe Val Ala Ser Glu Asn Ser Tyr Asn Asp Asp Asn Ile
                435                     440                     445
Asn Thr Pro Lys Glu Ile Asp Asp Thr Val Thr Ser Asn Asn Asn Tyr
        450                     455                     460
Glu Asn Asp Leu Asp Gln Val Ile Leu Asn Phe Asn Ser Glu Ser Ala
465                     470                     475                     480
```

```
Pro Gly Leu Ser Asp Glu Lys Leu Asn Leu Thr Ile Gln Asn Asp Ala
            485                 490                 495

Tyr Ile Pro Lys Tyr Asp Ser Asn Gly Thr Ser Asp Ile Glu Gln His
        500                 505                 510

Asp Val Asn Glu Leu Asn Val Phe Phe Tyr Leu Asp Ala Gln Lys Val
        515                 520                 525

Pro Glu Gly Glu Asn Asn Val Asn Leu Thr Ser Ser Ile Asp Thr Ala
    530                 535                 540

Leu Leu Glu Gln Pro Lys Ile Tyr Thr Phe Phe Ser Ser Glu Phe Ile
545                 550                 555                 560

Asn Asn Val Asn Lys Pro Val Gln Ala Ala Leu Phe Val Ser Trp Ile
                565                 570                 575

Gln Gln Val Leu Val Asp Phe Thr Thr Glu Ala Asn Gln Lys Ser Thr
            580                 585                 590

Val Asp Lys Ile Ala Asp Ile Ser Ile Val Val Pro Tyr Ile Gly Leu
        595                 600                 605

Ala Leu Asn Ile Gly Asn Glu Ala Gln Lys Gly Asn Phe Lys Asp Ala
    610                 615                 620

Leu Glu Leu Leu Gly Ala Gly Ile Leu Leu Glu Phe Glu Pro Glu Leu
625                 630                 635                 640

Leu Ile Pro Thr Ile Leu Val Phe Thr Ile Lys Ser Phe Leu Gly Ser
                645                 650                 655

Ser Asp Asn Lys Asn Lys Val Ile Lys Ala Ile Asn Asn Ala Leu Lys
            660                 665                 670

Glu Arg Asp Glu Lys Trp Lys Glu Val Tyr Ser Phe Ile Val Ser Asn
        675                 680                 685

Trp Met Thr Lys Ile Asn Thr Gln Phe Asn Lys Arg Lys Glu Gln Met
    690                 695                 700

Tyr Gln Ala Leu Gln Asn Gln Val Asn Ala Ile Lys Thr Ile Ile Glu
705                 710                 715                 720

Ser Lys Tyr Asn Ser Tyr Thr Leu Glu Glu Lys Asn Glu Leu Thr Asn
                725                 730                 735

Lys Tyr Asp Ile Lys Gln Ile Glu Asn Glu Leu Asn Gln Lys Val Ser
            740                 745                 750

Ile Ala Met Asn Asn Ile Asp Arg Phe Leu Thr Glu Ser Ser Ile Ser
        755                 760                 765

Tyr Leu Met Lys Ile Ile Asn Glu Val Lys Ile Asn Lys Leu Arg Glu
    770                 775                 780

Tyr Asp Glu Asn Val Lys Thr Tyr Leu Leu Asn Tyr Ile Ile Gln His
785                 790                 795                 800

Gly Ser Ile Leu Gly Glu Ser Gln Gln Glu Leu Asn Ser Met Val Thr
                805                 810                 815

Asp Thr Leu Asn Asn Ser Ile Pro Phe Lys Leu Ser Ser Tyr Thr Asp
            820                 825                 830

Asp Lys Ile Leu Ile Ser Tyr Phe Asn Lys Phe Phe Lys Arg Ile Lys
        835                 840                 845

Ser Ser Ser Val Leu Asn Met Arg Tyr Lys Asn Asp Lys Tyr Val Asp
    850                 855                 860

Thr Ser Gly Tyr Asp Ser Asn Ile Asn Ile Asn Gly Asp Val Tyr Lys
865                 870                 875                 880

Tyr Pro Thr Asn Lys Asn Gln Phe Gly Ile Tyr Asn Asp Lys Leu Ser
                885                 890                 895

Glu Val Asn Ile Ser Gln Asn Asp Tyr Ile Ile Tyr Asp Asn Lys Tyr
            900                 905                 910
```

Lys Asn Phe Ser Ile Ser Phe Trp Val Arg Ile Pro Asn Tyr Asp Asn
            915                 920                 925

Lys Ile Val Asn Val Asn Asn Glu Tyr Thr Ile Ile Asn Cys Met Arg
        930                 935                 940

Asp Asn Asn Ser Gly Trp Lys Val Ser Leu His Asn Glu Ile Ile
945                 950                 955                 960

Trp Thr Phe Glu Asp Asn Arg Gly Ile Asn Gln Lys Leu Ala Phe Asn
            965                 970                 975

Tyr Gly Asn Ala Asn Gly Ile Ser Asp Tyr Ile Asn Lys Trp Ile Phe
        980                 985                 990

Val Thr Ile Thr Asn Asp Arg Leu Gly Asp Ser Lys Leu Tyr Ile Asn
        995                 1000                1005

Gly Asn Leu Ile Asp Gln Lys Ser Ile Leu Asn Leu Gly Asn Ile His
    1010                1015                1020

Val Ser Asp Asn Ile Leu Phe Lys Ile Val Asn Cys Ser Tyr Thr Arg
1025                1030                1035                1040

Tyr Ile Gly Ile Arg Tyr Phe Asn Ile Phe Asp Lys Glu Leu Asp Glu
            1045                1050                1055

Thr Glu Ile Gln Thr Leu Tyr Ser Asn Glu Pro Asn Thr Asn Ile Leu
        1060                1065                1070

Lys Asp Phe Trp Gly Asn Tyr Leu Leu Tyr Asp Lys Glu Tyr Tyr Leu
        1075                1080                1085

Leu Asn Val Leu Lys Pro Asn Asn Phe Ile Asp Arg Arg Lys Asp Ser
    1090                1095                1100

Thr Leu Ser Ile Asn Asn Ile Arg Ser Thr Ile Leu Leu Ala Asn Arg
1105                1110                1115                1120

Leu Tyr Ser Gly Ile Lys Val Lys Ile Gln Arg Val Asn Asn Ser Ser
            1125                1130                1135

Thr Asn Asp Asn Leu Val Arg Lys Asn Asp Gln Val Tyr Ile Asn Phe
        1140                1145                1150

Val Ala Ser Lys Thr His Leu Phe Pro Leu Tyr Ala Asp Thr Ala Thr
    1155                1160                1165

Thr Asn Lys Glu Lys Thr Ile Lys Ile Ser Ser Ser Gly Asn Arg Phe
    1170                1175                1180

Asn Gln Val Val Val Met Asn Ser Val Gly Asn Cys Thr Met Asn Phe
1185                1190                1195                1200

Lys Asn Asn Asn Gly Asn Asn Ile Gly Leu Leu Gly Phe Lys Ala Asp
            1205                1210                1215

Thr Val Val Ala Ser Thr Trp Tyr Tyr Thr His Met Arg Asp His Thr
        1220                1225                1230

Asn Ser Asn Gly Cys Phe Trp Asn Phe Ile Ser Glu Glu His Gly Trp
        1235                1240                1245

Gln Glu Lys
    1250

<210> SEQ ID NO 2
<211> LENGTH: 1251
<212> TYPE: PRT
<213> ORGANISM: Clostridium butyricum

<400> SEQUENCE: 2

Met Pro Thr Ile Asn Ser Phe Asn Tyr Asn Asp Pro Val Asn Asp Arg
1               5                   10                  15

Thr Ile Leu Tyr Ile Lys Pro Gly Gly Cys Gln Gln Phe Tyr Lys Ser
            20                  25                  30

```
Phe Asn Ile Met Lys Asn Ile Trp Ile Ile Pro Glu Arg Asn Val Ile
         35                  40                  45

Gly Thr Ile Pro Gln Asp Phe Leu Pro Pro Thr Ser Leu Lys Asn Gly
     50                  55                  60

Asp Ser Ser Tyr Tyr Asp Pro Asn Tyr Leu Gln Ser Asp Gln Glu Lys
 65                  70                  75                  80

Asp Lys Phe Leu Lys Ile Val Thr Lys Ile Phe Asn Arg Ile Asn Asp
                 85                  90                  95

Asn Leu Ser Gly Arg Ile Leu Leu Glu Glu Leu Ser Lys Ala Asn Pro
            100                 105                 110

Tyr Leu Gly Asn Asp Asn Thr Pro Asp Gly Asp Phe Ile Ile Asn Asp
        115                 120                 125

Ala Ser Ala Val Pro Ile Gln Phe Ser Asn Gly Ser Gln Ser Ile Leu
    130                 135                 140

Leu Pro Asn Val Ile Ile Met Gly Ala Glu Pro Asp Leu Phe Glu Thr
145                 150                 155                 160

Asn Ser Ser Asn Ile Ser Leu Arg Asn Asn Tyr Met Pro Ser Asn His
                165                 170                 175

Gly Phe Gly Ser Ile Ala Ile Val Thr Phe Ser Pro Glu Tyr Ser Phe
            180                 185                 190

Arg Phe Lys Asp Asn Ser Met Asn Glu Phe Ile Gln Asp Pro Ala Leu
        195                 200                 205

Thr Leu Met His Glu Leu Ile His Ser Leu His Gly Leu Tyr Gly Ala
    210                 215                 220

Lys Gly Ile Thr Thr Lys Tyr Thr Ile Thr Gln Lys Gln Asn Pro Leu
225                 230                 235                 240

Ile Thr Asn Ile Arg Gly Thr Asn Ile Glu Glu Phe Leu Thr Phe Gly
                245                 250                 255

Gly Thr Asp Leu Asn Ile Ile Thr Ser Ala Gln Ser Asn Asp Ile Tyr
            260                 265                 270

Thr Asn Leu Leu Ala Asp Tyr Lys Lys Ile Ala Ser Lys Leu Ser Lys
        275                 280                 285

Val Gln Val Ser Asn Pro Leu Leu Asn Pro Tyr Lys Asp Val Phe Glu
    290                 295                 300

Ala Lys Tyr Gly Leu Asp Lys Asp Ala Ser Gly Ile Tyr Ser Val Asn
305                 310                 315                 320

Ile Asn Lys Phe Asn Asp Ile Phe Lys Lys Leu Tyr Ser Phe Thr Glu
                325                 330                 335

Phe Asp Leu Ala Thr Lys Phe Gln Val Lys Cys Arg Gln Thr Tyr Ile
            340                 345                 350

Gly Gln Tyr Lys Tyr Phe Lys Leu Ser Asn Leu Leu Asn Asp Ser Ile
        355                 360                 365

Tyr Asn Ile Ser Glu Gly Tyr Asn Ile Asn Asn Leu Lys Val Asn Phe
    370                 375                 380

Arg Gly Gln Asn Ala Asn Leu Asn Pro Arg Ile Ile Thr Pro Ile Thr
385                 390                 395                 400

Gly Arg Gly Leu Val Lys Lys Ile Ile Arg Phe Cys Lys Asn Ile Val
                405                 410                 415

Ser Val Lys Gly Ile Arg Lys Ser Ile Cys Ile Glu Ile Asn Asn Gly
            420                 425                 430

Glu Leu Phe Phe Val Ala Ser Glu Asn Ser Tyr Asn Asp Asp Asn Ile
        435                 440                 445

Asn Thr Pro Lys Glu Ile Asp Asp Thr Val Thr Ser Asn Asn Asn Tyr
```

-continued

```
            450                 455                 460
Glu Asn Asp Leu Asp Gln Val Ile Leu Asn Phe Asn Ser Glu Ser Ala
465                 470                 475                 480

Pro Gly Leu Ser Asp Glu Lys Leu Asn Leu Thr Ile Gln Asn Asp Ala
                485                 490                 495

Tyr Ile Pro Lys Tyr Asp Ser Asn Gly Thr Ser Asp Ile Glu Gln His
                500                 505                 510

Asp Val Asn Glu Leu Asn Val Phe Phe Tyr Leu Asp Ala Gln Lys Val
            515                 520                 525

Pro Glu Gly Glu Asn Asn Val Asn Leu Thr Ser Ser Ile Asp Thr Ala
            530                 535                 540

Leu Leu Glu Gln Pro Lys Ile Tyr Thr Phe Phe Ser Ser Glu Phe Ile
545                 550                 555                 560

Asn Asn Val Asn Lys Pro Val Gln Ala Ala Leu Phe Val Gly Trp Ile
                565                 570                 575

Gln Gln Val Leu Val Asp Phe Thr Thr Glu Ala Asn Gln Lys Ser Thr
            580                 585                 590

Val Asp Lys Ile Ala Asp Ile Ser Ile Val Pro Tyr Ile Gly Leu
            595                 600                 605

Ala Leu Asn Ile Gly Asn Glu Ala Gln Lys Gly Asn Phe Lys Asp Ala
610                 615                 620

Leu Glu Leu Leu Gly Ala Gly Ile Leu Leu Glu Phe Glu Pro Glu Leu
625                 630                 635                 640

Leu Ile Pro Thr Ile Leu Val Phe Thr Ile Lys Ser Phe Leu Gly Ser
                645                 650                 655

Ser Asp Asn Lys Asn Lys Val Ile Lys Ala Ile Asn Asn Ala Leu Lys
            660                 665                 670

Glu Arg Asp Glu Lys Trp Lys Glu Val Tyr Ser Phe Ile Val Ser Asn
            675                 680                 685

Trp Met Thr Lys Ile Asn Thr Gln Phe Asn Lys Arg Lys Glu Gln Met
            690                 695                 700

Tyr Gln Ala Leu Gln Asn Gln Val Asn Ala Leu Lys Ala Ile Ile Glu
705                 710                 715                 720

Ser Lys Tyr Asn Ser Tyr Thr Leu Glu Glu Lys Asn Glu Leu Thr Asn
                725                 730                 735

Lys Tyr Asp Ile Glu Gln Ile Glu Asn Glu Leu Asn Gln Lys Val Ser
            740                 745                 750

Ile Ala Met Asn Asn Ile Asp Arg Phe Leu Thr Glu Ser Ser Ile Ser
            755                 760                 765

Tyr Leu Met Lys Leu Ile Asn Glu Val Lys Ile Asn Lys Leu Arg Glu
770                 775                 780

Tyr Asp Glu Asn Val Lys Thr Tyr Leu Leu Asp Tyr Ile Ile Lys His
785                 790                 795                 800

Gly Ser Ile Leu Gly Glu Ser Gln Gln Glu Leu Asn Ser Met Val Ile
                805                 810                 815

Asp Thr Leu Asn Asn Ser Ile Pro Phe Lys Leu Ser Ser Tyr Thr Asp
            820                 825                 830

Asp Lys Ile Leu Ile Ser Tyr Phe Asn Lys Phe Phe Lys Arg Ile Lys
            835                 840                 845

Ser Ser Ser Val Leu Asn Met Arg Tyr Lys Asn Asp Lys Tyr Val Asp
            850                 855                 860

Thr Ser Gly Tyr Asp Ser Asn Ile Asn Ile Asn Gly Asp Val Tyr Lys
865                 870                 875                 880
```

Tyr Pro Thr Asn Lys Asn Gln Phe Gly Ile Tyr Asn Asp Lys Leu Ser
            885                 890                 895

Glu Val Asn Ile Ser Gln Asn Asp Tyr Ile Ile Tyr Asp Asn Lys Tyr
        900                 905                 910

Lys Asn Phe Ser Ile Ser Phe Trp Val Arg Ile Pro Asn Tyr Asp Asn
    915                 920                 925

Lys Ile Val Asn Val Asn Asn Glu Tyr Thr Ile Ile Asn Cys Met Arg
930                 935                 940

Asp Asn Asn Ser Gly Trp Lys Val Ser Leu Asn His Asn Glu Ile Ile
945                 950                 955                 960

Trp Thr Leu Gln Asp Asn Ser Gly Ile Asn Gln Lys Leu Ala Phe Asn
            965                 970                 975

Tyr Gly Asn Ala Asn Gly Ile Ser Asp Tyr Ile Asn Lys Trp Ile Phe
        980                 985                 990

Val Thr Ile Thr Asn Asp Arg Leu Gly Asp Ser Lys Leu Tyr Ile Asn
    995                 1000                1005

Gly Asn Leu Ile Asp Lys Lys Ser Ile Leu Asn Leu Gly Asn Ile His
    1010                1015                1020

Val Ser Asp Asn Ile Leu Phe Lys Ile Val Asn Cys Ser Tyr Thr Arg
1025                1030                1035                1040

Tyr Ile Gly Ile Arg Tyr Phe Asn Ile Phe Asp Lys Glu Leu Asp Glu
            1045                1050                1055

Thr Glu Ile Gln Thr Leu Tyr Asn Asn Glu Pro Asn Ala Asn Ile Leu
        1060                1065                1070

Lys Asp Phe Trp Gly Asn Tyr Leu Leu Tyr Asp Lys Glu Tyr Tyr Leu
    1075                1080                1085

Leu Asn Val Leu Lys Pro Asn Asn Phe Ile Asn Arg Arg Thr Asp Ser
    1090                1095                1100

Thr Leu Ser Ile Asn Asn Ile Arg Ser Thr Ile Leu Leu Ala Asn Arg
1105                1110                1115                1120

Leu Tyr Ser Gly Ile Lys Val Lys Ile Gln Arg Val Asn Asn Ser Ser
            1125                1130                1135

Thr Asn Asp Asn Leu Val Arg Lys Asn Asp Gln Val Tyr Ile Asn Phe
        1140                1145                1150

Val Ala Ser Lys Thr His Leu Leu Pro Leu Tyr Ala Asp Thr Ala Thr
    1155                1160                1165

Thr Asn Lys Glu Lys Thr Ile Lys Ile Ser Ser Ser Gly Asn Arg Phe
    1170                1175                1180

Asn Gln Val Val Val Met Asn Ser Val Gly Asn Cys Thr Met Asn Phe
1185                1190                1195                1200

Lys Asn Asn Asn Gly Asn Asn Ile Gly Leu Leu Gly Phe Lys Ala Asp
            1205                1210                1215

Thr Val Val Ala Ser Thr Trp Tyr Tyr Thr His Met Arg Asp Asn Thr
        1220                1225                1230

Asn Ser Asn Gly Phe Phe Trp Asn Phe Ile Ser Glu Glu His Gly Trp
    1235                1240                1245

Gln Glu Lys
    1250

<210> SEQ ID NO 3
<211> LENGTH: 40
<212> TYPE: DNA
<213> ORGANISM: Artificial Sequence
<220> FEATURE:
<223> OTHER INFORMATION: Description of Artificial Sequence: Synthetic
      Primer

```
<400> SEQUENCE: 3
gtatattaaa ccgggcggca gccaggagtt ttataaaagc                                40

<210> SEQ ID NO 4
<211> LENGTH: 40
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 4
gcttttataa aactcctggc tgccgcccgg tttaatatac                                40

<210> SEQ ID NO 5
<211> LENGTH: 39
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 5
gtaccaaatt tcaggtgaag agccgccaaa cctacatcg                                 39

<210> SEQ ID NO 6
<211> LENGTH: 39
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 6
cgatgtaggt ttggcggctc ttcacctgaa atttggtac                                 39

<210> SEQ ID NO 7
<211> LENGTH: 844
<212> TYPE: PRT
<213> ORGANISM: Clostridium botulinum

<400> SEQUENCE: 7
```

Pro Lys Ile Asn Ser Phe Asn Tyr Asn Asp Pro Val Asn Asp Arg Thr
 1               5                  10                  15

Ile Leu Tyr Ile Lys Pro Gly Gly Ser Gln Glu Phe Tyr Lys Ser Phe
             20                  25                  30

Asn Ile Met Lys Asn Ile Trp Ile Ile Pro Glu Arg Asn Val Ile Gly
         35                  40                  45

Thr Thr Pro Gln Asp Phe His Pro Pro Thr Ser Leu Lys Asn Gly Asp
     50                  55                  60

Ser Ser Tyr Tyr Asp Pro Asn Tyr Leu Gln Ser Asp Glu Glu Lys Asp
 65                  70                  75                  80

Arg Phe Leu Lys Ile Val Thr Lys Ile Phe Asn Arg Ile Asn Asn Asn
                 85                  90                  95

Leu Ser Gly Gly Ile Leu Leu Glu Glu Leu Ser Lys Ala Asn Pro Tyr
            100                 105                 110

Leu Gly Asn Asp Asn Thr Pro Asp Asn Gln Phe His Ile Gly Asp Ala
        115                 120                 125

Ser Ala Val Glu Ile Lys Phe Ser Asn Gly Ser Gln Asp Ile Leu Leu
    130                 135                 140

Pro Asn Val Ile Ile Met Gly Ala Glu Pro Asp Leu Phe Glu Thr Asn

-continued

```
            145                 150                 155                 160
        Ser Ser Asn Ile Ser Leu Arg Asn Asn Tyr Met Pro Ser Asn His Arg
                        165                 170                 175

Phe Gly Ser Ile Ala Ile Val Thr Phe Ser Pro Glu Tyr Ser Phe Arg
                        180                 185                 190

Phe Asn Asp Asn Cys Met Asn Glu Phe Ile Gln Asp Pro Ala Leu Thr
                        195                 200                 205

Leu Met His Glu Leu Ile His Ser Leu His Gly Leu Tyr Gly Ala Lys
                        210                 215                 220

Gly Ile Thr Thr Lys Tyr Thr Ile Thr Gln Lys Gln Asn Pro Leu Ile
        225                 230                 235                 240

Thr Asn Ile Arg Gly Thr Asn Ile Glu Glu Phe Leu Thr Phe Gly Gly
                        245                 250                 255

Thr Asp Leu Asn Ile Ile Thr Ser Ala Gln Ser Asn Asp Ile Tyr Thr
                        260                 265                 270

Asn Leu Leu Ala Asp Tyr Lys Lys Ile Ala Ser Lys Leu Ser Lys Val
                        275                 280                 285

Gln Val Ser Asn Pro Leu Leu Asn Pro Tyr Lys Asp Val Phe Glu Ala
                        290                 295                 300

Lys Tyr Gly Leu Asp Lys Asp Ala Ser Gly Ile Tyr Ser Val Asn Ile
        305                 310                 315                 320

Asn Lys Phe Asn Asp Ile Phe Lys Lys Leu Tyr Ser Phe Thr Glu Phe
                        325                 330                 335

Asp Leu Arg Thr Lys Phe Gln Val Lys Ser Arg Gln Thr Tyr Ile Gly
                        340                 345                 350

Gln Tyr Lys Tyr Phe Lys Leu Ser Asn Leu Leu Asn Asp Ser Ile Tyr
                        355                 360                 365

Asn Ile Ser Glu Gly Tyr Asn Ile Asn Asn Leu Lys Val Asn Phe Arg
                        370                 375                 380

Gly Gln Asn Ala Asn Leu Asn Pro Arg Ile Ile Thr Pro Ile Thr Gly
        385                 390                 395                 400

Arg Gly Leu Val Lys Lys Ile Ile Arg Phe Cys Lys Asn Ile Val Ser
                        405                 410                 415

Val Lys Gly Ile Arg Lys Ser Ile Cys Ile Glu Ile Asn Asn Gly Glu
                        420                 425                 430

Leu Phe Phe Val Ala Ser Glu Asn Ser Tyr Asn Asp Asp Asn Ile Asn
                        435                 440                 445

Thr Pro Lys Glu Ile Asp Asp Thr Val Thr Ser Asn Asn Asn Tyr Glu
                        450                 455                 460

Asn Asp Leu Asp Gln Val Ile Leu Asn Phe Asn Ser Glu Ser Ala Pro
        465                 470                 475                 480

Gly Leu Ser Asp Glu Lys Leu Asn Leu Thr Ile Gln Asn Asp Ala Tyr
                        485                 490                 495

Ile Pro Lys Tyr Asp Ser Asn Gly Thr Ser Asp Ile Glu Gln His Asp
                        500                 505                 510

Val Asn Glu Leu Asn Val Phe Phe Tyr Leu Asp Ala Gln Lys Val Pro
                        515                 520                 525

Glu Gly Glu Asn Asn Val Asn Leu Thr Ser Ser Ile Asp Thr Ala Leu
                        530                 535                 540

Leu Glu Gln Pro Lys Ile Tyr Thr Phe Phe Ser Ser Glu Phe Ile Asn
        545                 550                 555                 560

Asn Val Asn Lys Pro Val Gln Ala Ala Leu Phe Val Ser Trp Ile Gln
                        565                 570                 575
```

-continued

Gln Val Leu Val Asp Phe Thr Thr Glu Ala Asn Gln Lys Ser Thr Val
                580                 585                 590

Asp Lys Ile Ala Asp Ile Ser Ile Val Val Pro Tyr Ile Gly Leu Ala
            595                 600                 605

Leu Asn Ile Gly Asn Glu Ala Gln Lys Gly Asn Phe Lys Asp Ala Leu
        610                 615                 620

Glu Leu Leu Gly Ala Gly Ile Leu Leu Glu Phe Glu Pro Glu Leu Leu
625                 630                 635                 640

Ile Pro Thr Ile Leu Val Phe Thr Ile Lys Ser Phe Leu Gly Ser Ser
                645                 650                 655

Asp Asn Lys Asn Lys Val Ile Lys Ala Ile Asn Asn Ala Leu Lys Glu
            660                 665                 670

Arg Asp Glu Lys Trp Lys Glu Val Tyr Ser Phe Ile Val Ser Asn Trp
        675                 680                 685

Met Thr Lys Ile Asn Thr Gln Phe Asn Lys Arg Lys Glu Gln Met Tyr
        690                 695                 700

Gln Ala Leu Gln Asn Gln Val Asn Ala Ile Lys Thr Ile Ile Glu Ser
705                 710                 715                 720

Lys Tyr Asn Ser Tyr Thr Leu Glu Glu Lys Asn Glu Leu Thr Asn Lys
                725                 730                 735

Tyr Asp Ile Lys Gln Ile Glu Asn Glu Leu Asn Gln Lys Val Ser Ile
            740                 745                 750

Ala Met Asn Asn Ile Asp Arg Phe Leu Thr Glu Ser Ser Ile Ser Tyr
        755                 760                 765

Leu Met Lys Ile Ile Asn Glu Val Lys Ile Asn Lys Leu Arg Glu Tyr
770                 775                 780

Asp Glu Asn Val Lys Thr Tyr Leu Leu Asn Tyr Ile Ile Gln His Gly
785                 790                 795                 800

Ser Ile Leu Gly Glu Ser Gln Gln Glu Leu Asn Ser Met Val Thr Asp
                805                 810                 815

Thr Leu Asn Asn Ser Ile Pro Phe Lys Leu Ser Ser Tyr Thr Asp Asp
            820                 825                 830

Lys Ile Leu Ile Ser Tyr Phe Asn Lys Phe Phe Lys
        835                 840

<210> SEQ ID NO 8
<211> LENGTH: 844
<212> TYPE: PRT
<213> ORGANISM: Clostridium botulinum

<400> SEQUENCE: 8

Pro Lys Ile Asn Ser Phe Asn Tyr Asn Asp Pro Val Asn Asp Arg Thr
1               5                   10                  15

Ile Leu Tyr Ile Lys Pro Gly Gly Ser Gln Glu Phe Tyr Lys Ser Phe
            20                  25                  30

Asn Ile Met Lys Asn Ile Trp Ile Ile Pro Glu Arg Asn Val Ile Gly
        35                  40                  45

Thr Thr Pro Gln Asp Phe His Pro Pro Thr Ser Leu Lys Asn Gly Asp
    50                  55                  60

Ser Ser Tyr Tyr Asp Pro Asn Tyr Leu Gln Ser Asp Glu Glu Lys Asp
65                  70                  75                  80

Arg Phe Leu Lys Ile Val Thr Lys Ile Phe Asn Arg Ile Asn Asn Asn
                85                  90                  95

Leu Ser Gly Gly Ile Leu Leu Glu Glu Leu Ser Lys Ala Asn Pro Tyr
            100                 105                 110

-continued

Leu Gly Asn Asp Asn Thr Pro Asp Asn Gln Phe His Ile Gly Asp Ala
        115                 120                 125

Ser Ala Val Glu Ile Lys Phe Ser Asn Gly Ser Gln Asp Ile Leu Leu
130                 135                 140

Pro Asn Val Ile Ile Met Gly Ala Glu Pro Asp Leu Phe Glu Thr Asn
145                 150                 155                 160

Ser Ser Asn Ile Ser Leu Arg Asn Asn Tyr Met Pro Ser Asn His Arg
                165                 170                 175

Phe Gly Ser Ile Ala Ile Val Thr Phe Ser Pro Glu Tyr Ser Phe Arg
            180                 185                 190

Phe Asn Asp Asn Cys Met Asn Glu Phe Ile Gln Asp Pro Ala Leu Thr
        195                 200                 205

Leu Met His Gln Leu Ile Tyr Ser Leu His Gly Leu Tyr Gly Ala Lys
210                 215                 220

Gly Ile Thr Thr Lys Tyr Thr Ile Thr Gln Lys Gln Asn Pro Leu Ile
225                 230                 235                 240

Thr Asn Ile Arg Gly Thr Asn Ile Glu Glu Phe Leu Thr Phe Gly Gly
                245                 250                 255

Thr Asp Leu Asn Ile Ile Thr Ser Ala Gln Ser Asn Asp Ile Tyr Thr
            260                 265                 270

Asn Leu Leu Ala Asp Tyr Lys Lys Ile Ala Ser Lys Leu Ser Lys Val
        275                 280                 285

Gln Val Ser Asn Pro Leu Leu Asn Pro Tyr Lys Asp Val Phe Glu Ala
290                 295                 300

Lys Tyr Gly Leu Asp Lys Asp Ala Ser Gly Ile Tyr Ser Val Asn Ile
305                 310                 315                 320

Asn Lys Phe Asn Asp Ile Phe Lys Lys Leu Tyr Ser Phe Thr Glu Phe
                325                 330                 335

Asp Leu Arg Thr Lys Phe Gln Val Lys Ser Arg Gln Thr Tyr Ile Gly
            340                 345                 350

Gln Tyr Lys Tyr Phe Lys Leu Ser Asn Leu Leu Asn Asp Ser Ile Tyr
        355                 360                 365

Asn Ile Ser Glu Gly Tyr Asn Ile Asn Asn Leu Lys Val Asn Phe Arg
370                 375                 380

Gly Gln Asn Ala Asn Leu Asn Pro Arg Ile Ile Thr Pro Ile Thr Gly
385                 390                 395                 400

Arg Gly Leu Val Lys Lys Ile Ile Arg Phe Cys Lys Asn Ile Val Ser
                405                 410                 415

Val Lys Gly Ile Arg Lys Ser Ile Cys Ile Glu Ile Asn Gly Glu
            420                 425                 430

Leu Phe Phe Val Ala Ser Glu Asn Ser Tyr Asn Asp Asp Asn Ile Asn
        435                 440                 445

Thr Pro Lys Glu Ile Asp Asp Thr Val Thr Ser Asn Asn Asn Tyr Glu
450                 455                 460

Asn Asp Leu Asp Gln Val Ile Leu Asn Phe Asn Ser Glu Ser Ala Pro
465                 470                 475                 480

Gly Leu Ser Asp Glu Lys Leu Asn Leu Thr Ile Gln Asn Asp Ala Tyr
                485                 490                 495

Ile Pro Lys Tyr Asp Ser Asn Gly Thr Ser Asp Ile Glu Gln His Asp
            500                 505                 510

Val Asn Glu Leu Asn Val Phe Phe Tyr Leu Asp Ala Gln Lys Val Pro
        515                 520                 525

Glu Gly Glu Asn Asn Val Asn Leu Thr Ser Ser Ile Asp Thr Ala Leu
530                 535                 540

```
Leu Glu Gln Pro Lys Ile Tyr Thr Phe Phe Ser Ser Glu Phe Ile Asn
545                 550                 555                 560

Asn Val Asn Lys Pro Val Gln Ala Ala Leu Phe Val Ser Trp Ile Gln
            565                 570                 575

Gln Val Leu Val Asp Phe Thr Thr Glu Ala Asn Gln Lys Ser Thr Val
        580                 585                 590

Asp Lys Ile Ala Asp Ile Ser Ile Val Val Pro Tyr Ile Gly Leu Ala
    595                 600                 605

Leu Asn Ile Gly Asn Glu Ala Gln Lys Gly Asn Phe Lys Asp Ala Leu
610                 615                 620

Glu Leu Leu Gly Ala Gly Ile Leu Leu Glu Phe Glu Pro Glu Leu Leu
625                 630                 635                 640

Ile Pro Thr Ile Leu Val Phe Thr Ile Lys Ser Phe Leu Gly Ser Ser
            645                 650                 655

Asp Asn Lys Asn Lys Val Ile Lys Ala Ile Asn Asn Ala Leu Lys Glu
        660                 665                 670

Arg Asp Glu Lys Trp Lys Glu Val Tyr Ser Phe Ile Val Ser Asn Trp
    675                 680                 685

Met Thr Lys Ile Asn Thr Gln Phe Asn Lys Arg Lys Glu Gln Met Tyr
690                 695                 700

Gln Ala Leu Gln Asn Gln Val Asn Ala Ile Lys Thr Ile Ile Glu Ser
705                 710                 715                 720

Lys Tyr Asn Ser Tyr Thr Leu Glu Glu Lys Asn Glu Leu Thr Asn Lys
            725                 730                 735

Tyr Asp Ile Lys Gln Ile Glu Asn Glu Leu Asn Gln Lys Val Ser Ile
        740                 745                 750

Ala Met Asn Asn Ile Asp Arg Phe Leu Thr Glu Ser Ser Ile Ser Tyr
    755                 760                 765

Leu Met Lys Ile Ile Asn Glu Val Lys Ile Asn Lys Leu Arg Glu Tyr
770                 775                 780

Asp Glu Asn Val Lys Thr Tyr Leu Leu Asn Tyr Ile Ile Gln His Gly
785                 790                 795                 800

Ser Ile Leu Gly Glu Ser Gln Gln Glu Leu Asn Ser Met Val Thr Asp
            805                 810                 815

Thr Leu Asn Asn Ser Ile Pro Phe Lys Leu Ser Ser Tyr Thr Asp Asp
        820                 825                 830

Lys Ile Leu Ile Ser Tyr Phe Asn Lys Phe Phe Lys
    835                 840

<210> SEQ ID NO 9
<211> LENGTH: 1250
<212> TYPE: PRT
<213> ORGANISM: Clostridium botulinum

<400> SEQUENCE: 9

Pro Lys Ile Asn Ser Phe Asn Tyr Asn Asp Pro Val Asn Asp Arg Thr
1               5                   10                  15

Ile Leu Tyr Ile Lys Pro Gly Gly Ser Gln Glu Phe Tyr Lys Ser Phe
            20                  25                  30

Asn Ile Met Lys Asn Ile Trp Ile Ile Pro Glu Arg Asn Val Ile Gly
        35                  40                  45

Thr Thr Pro Gln Asp Phe His Pro Pro Thr Ser Leu Lys Asn Gly Asp
    50                  55                  60

Ser Ser Tyr Tyr Asp Pro Asn Tyr Leu Gln Ser Asp Glu Glu Lys Asp
65                  70                  75                  80
```

```
Arg Phe Leu Lys Ile Val Thr Lys Ile Phe Asn Arg Ile Asn Asn Asn
             85                  90                  95
Leu Ser Gly Gly Ile Leu Leu Glu Glu Leu Ser Lys Ala Asn Pro Tyr
            100                 105                 110
Leu Gly Asn Asp Asn Thr Pro Asp Asn Gln Phe His Ile Gly Asp Ala
            115                 120                 125
Ser Ala Val Glu Ile Lys Phe Ser Asn Gly Ser Gln Asp Ile Leu Leu
130                 135                 140
Pro Asn Val Ile Ile Met Gly Ala Glu Pro Asp Leu Phe Glu Thr Asn
145                 150                 155                 160
Ser Ser Asn Ile Ser Leu Arg Asn Asn Tyr Met Pro Ser Asn His Arg
                165                 170                 175
Phe Gly Ser Ile Ala Ile Val Thr Phe Ser Pro Glu Tyr Ser Phe Arg
            180                 185                 190
Phe Asn Asp Asn Cys Met Asn Glu Phe Ile Gln Asp Pro Ala Leu Thr
            195                 200                 205
Leu Met His Gln Leu Ile Tyr Ser Leu His Gly Leu Tyr Gly Ala Lys
        210                 215                 220
Gly Ile Thr Thr Lys Tyr Thr Ile Thr Gln Lys Gln Asn Pro Leu Ile
225                 230                 235                 240
Thr Asn Ile Arg Gly Thr Asn Ile Glu Glu Phe Leu Thr Phe Gly Gly
                245                 250                 255
Thr Asp Leu Asn Ile Ile Thr Ser Ala Gln Ser Asn Asp Ile Tyr Thr
            260                 265                 270
Asn Leu Leu Ala Asp Tyr Lys Lys Ile Ala Ser Lys Leu Ser Lys Val
        275                 280                 285
Gln Val Ser Asn Pro Leu Leu Asn Pro Tyr Lys Asp Val Phe Glu Ala
    290                 295                 300
Lys Tyr Gly Leu Asp Lys Asp Ala Ser Gly Ile Tyr Ser Val Asn Ile
305                 310                 315                 320
Asn Lys Phe Asn Asp Ile Phe Lys Lys Leu Tyr Ser Phe Thr Glu Phe
                325                 330                 335
Asp Leu Arg Thr Lys Phe Gln Val Lys Ser Arg Gln Thr Tyr Ile Gly
            340                 345                 350
Gln Tyr Lys Tyr Phe Lys Leu Ser Asn Leu Leu Asn Asp Ser Ile Tyr
        355                 360                 365
Asn Ile Ser Glu Gly Tyr Asn Ile Asn Asn Leu Lys Val Asn Phe Arg
    370                 375                 380
Gly Gln Asn Ala Asn Leu Asn Pro Arg Ile Ile Thr Pro Ile Thr Gly
385                 390                 395                 400
Arg Gly Leu Val Lys Lys Ile Ile Arg Phe Cys Lys Asn Ile Val Ser
                405                 410                 415
Val Lys Gly Ile Arg Lys Ser Ile Cys Ile Glu Ile Asn Asn Gly Glu
            420                 425                 430
Leu Phe Phe Val Ala Ser Glu Asn Ser Tyr Asn Asp Asp Asn Ile Asn
        435                 440                 445
Thr Pro Lys Glu Ile Asp Asp Thr Val Thr Ser Asn Asn Asn Tyr Glu
    450                 455                 460
Asn Asp Leu Asp Gln Val Ile Leu Asn Phe Asn Ser Glu Ser Ala Pro
465                 470                 475                 480
Gly Leu Ser Asp Glu Lys Leu Asn Leu Thr Ile Gln Asn Asp Ala Tyr
                485                 490                 495
Ile Pro Lys Tyr Asp Ser Asn Gly Thr Ser Asp Ile Glu Gln His Asp
```

```
                500             505             510
Val Asn Glu Leu Asn Val Phe Phe Tyr Leu Asp Ala Gln Lys Val Pro
        515                 520             525

Glu Gly Glu Asn Asn Val Asn Leu Thr Ser Ser Ile Asp Thr Ala Leu
    530                 535             540

Leu Glu Gln Pro Lys Ile Tyr Thr Phe Phe Ser Ser Glu Phe Ile Asn
545             550                 555             560

Asn Val Asn Lys Pro Val Gln Ala Ala Leu Phe Val Ser Trp Ile Gln
            565             570             575

Gln Val Leu Val Asp Phe Thr Thr Glu Ala Asn Gln Lys Ser Thr Val
        580                 585             590

Asp Lys Ile Ala Asp Ile Ser Ile Val Val Pro Tyr Ile Gly Leu Ala
        595             600             605

Leu Asn Ile Gly Asn Glu Ala Gln Lys Gly Asn Phe Lys Asp Ala Leu
    610             615             620

Glu Leu Leu Gly Ala Gly Ile Leu Leu Glu Phe Glu Pro Glu Leu Leu
625             630             635             640

Ile Pro Thr Ile Leu Val Phe Thr Ile Lys Ser Phe Leu Gly Ser Ser
            645             650             655

Asp Asn Lys Asn Lys Val Ile Lys Ala Ile Asn Asn Ala Leu Lys Glu
            660             665             670

Arg Asp Glu Lys Trp Lys Glu Val Tyr Ser Phe Ile Val Ser Asn Trp
    675             680             685

Met Thr Lys Ile Asn Thr Gln Phe Asn Lys Arg Lys Glu Gln Met Tyr
    690             695             700

Gln Ala Leu Gln Asn Gln Val Asn Ala Ile Lys Thr Ile Ile Glu Ser
705             710             715             720

Lys Tyr Asn Ser Tyr Thr Leu Glu Glu Lys Asn Glu Leu Thr Asn Lys
            725             730             735

Tyr Asp Ile Lys Gln Ile Glu Asn Glu Leu Asn Gln Lys Val Ser Ile
            740             745             750

Ala Met Asn Asn Ile Asp Arg Phe Leu Thr Glu Ser Ser Ile Ser Tyr
    755             760             765

Leu Met Lys Ile Ile Asn Glu Val Lys Ile Asn Lys Leu Arg Glu Tyr
    770             775             780

Asp Glu Asn Val Lys Thr Tyr Leu Leu Asn Tyr Ile Ile Gln His Gly
785             790             795             800

Ser Ile Leu Gly Glu Ser Gln Gln Glu Leu Asn Ser Met Val Thr Asp
            805             810             815

Thr Leu Asn Asn Ser Ile Pro Phe Lys Leu Ser Ser Tyr Thr Asp Asp
            820             825             830

Lys Ile Leu Ile Ser Tyr Phe Asn Lys Phe Phe Lys Arg Ile Lys Ser
        835             840             845

Ser Ser Val Leu Asn Met Arg Tyr Lys Asn Asp Lys Tyr Val Asp Thr
        850             855             860

Ser Gly Tyr Asp Ser Asn Ile Asn Ile Asn Gly Asp Val Tyr Lys Tyr
865             870             875             880

Pro Thr Asn Lys Asn Gln Phe Gly Ile Tyr Asn Asp Lys Leu Ser Glu
            885             890             895

Val Asn Ile Ser Gln Asn Asp Tyr Ile Ile Tyr Asp Asn Lys Tyr Lys
            900             905             910

Asn Phe Ser Ile Ser Phe Trp Val Arg Ile Pro Asn Tyr Asp Asn Lys
        915             920             925
```

```
Ile Val Asn Val Asn Asn Glu Tyr Thr Ile Ile Asn Cys Met Arg Asp
            930                 935                 940

Asn Asn Ser Gly Trp Lys Val Ser Leu Asn His Asn Glu Ile Ile Trp
945                 950                 955                 960

Thr Phe Glu Asp Asn Arg Gly Ile Asn Gln Lys Leu Ala Phe Asn Tyr
                965                 970                 975

Gly Asn Ala Asn Gly Ile Ser Asp Tyr Ile Asn Lys Trp Ile Phe Val
            980                 985                 990

Thr Ile Thr Asn Asp Arg Leu Gly Asp Ser Lys Leu Tyr Ile Asn Gly
        995                 1000                1005

Asn Leu Ile Asp Gln Lys Ser Ile Leu Asn Leu Gly Asn Ile His Val
    1010                1015                1020

Ser Asp Asn Ile Leu Phe Lys Ile Val Asn Cys Ser Tyr Thr Arg Tyr
1025                1030                1035                1040

Ile Gly Ile Arg Tyr Phe Asn Ile Phe Asp Lys Glu Leu Asp Glu Thr
                1045                1050                1055

Glu Ile Gln Thr Leu Tyr Ser Asn Glu Pro Asn Thr Asn Ile Leu Lys
            1060                1065                1070

Asp Phe Trp Gly Asn Tyr Leu Leu Tyr Asp Lys Glu Tyr Tyr Leu Leu
        1075                1080                1085

Asn Val Leu Lys Pro Asn Asn Phe Ile Asp Arg Arg Lys Asp Ser Thr
    1090                1095                1100

Leu Ser Ile Asn Asn Ile Arg Ser Thr Ile Leu Leu Ala Asn Arg Leu
1105                1110                1115                1120

Tyr Ser Gly Ile Lys Val Lys Ile Gln Arg Val Asn Asn Ser Ser Thr
                1125                1130                1135

Asn Asp Asn Leu Val Arg Lys Asn Asp Gln Val Tyr Ile Asn Phe Val
            1140                1145                1150

Ala Ser Lys Thr His Leu Phe Pro Leu Tyr Ala Asp Thr Ala Thr Thr
        1155                1160                1165

Asn Lys Glu Lys Thr Ile Lys Ile Ser Ser Ser Gly Asn Arg Phe Asn
    1170                1175                1180

Gln Val Val Val Met Asn Ser Val Gly Asn Cys Thr Met Asn Phe Lys
1185                1190                1195                1200

Asn Asn Asn Gly Asn Asn Ile Gly Leu Leu Gly Phe Lys Ala Asp Thr
                1205                1210                1215

Val Val Ala Ser Thr Leu Phe Tyr Thr His Met Arg Asp His Thr Asn
            1220                1225                1230

Ser Asn Gly Cys Phe Trp Asn Phe Ile Ser Glu His Gly Trp Gln
        1235                1240                1245

Glu Lys
    1250

<210> SEQ ID NO 10
<211> LENGTH: 1065
<212> TYPE: PRT
<213> ORGANISM: Clostridium botulinum

<400> SEQUENCE: 10

Pro Lys Ile Asn Ser Phe Asn Tyr Asn Asp Pro Val Asn Asp Arg Thr
1               5                   10                  15

Ile Leu Tyr Ile Lys Pro Gly Gly Ser Gln Glu Phe Tyr Lys Ser Phe
            20                  25                  30

Asn Ile Met Lys Asn Ile Trp Ile Ile Pro Glu Arg Asn Val Ile Gly
        35                  40                  45
```

```
Thr Thr Pro Gln Asp Phe His Pro Pro Thr Ser Leu Lys Asn Gly Asp
    50                  55                  60

Ser Ser Tyr Tyr Asp Pro Asn Tyr Leu Gln Ser Asp Glu Glu Lys Asp
65              70                  75                  80

Arg Phe Leu Lys Ile Val Thr Lys Ile Phe Asn Arg Ile Asn Asn Asn
                85                  90                  95

Leu Ser Gly Gly Ile Leu Leu Glu Glu Leu Ser Lys Ala Asn Pro Tyr
            100                 105                 110

Leu Gly Asn Asp Asn Thr Pro Asp Asn Gln Phe His Ile Gly Asp Ala
            115                 120                 125

Ser Ala Val Glu Ile Lys Phe Ser Asn Gly Ser Gln Asp Ile Leu Leu
        130                 135                 140

Pro Asn Val Ile Ile Met Gly Ala Glu Pro Asp Leu Phe Glu Thr Asn
145                 150                 155                 160

Ser Ser Asn Ile Ser Leu Arg Asn Asn Tyr Met Pro Ser Asn His Arg
                165                 170                 175

Phe Gly Ser Ile Ala Ile Val Thr Phe Ser Pro Glu Tyr Ser Phe Arg
            180                 185                 190

Phe Asn Asp Asn Cys Met Asn Glu Phe Ile Gln Asp Pro Ala Leu Thr
            195                 200                 205

Leu Met His Gln Leu Ile Tyr Ser Leu His Gly Leu Tyr Gly Ala Lys
    210                 215                 220

Gly Ile Thr Thr Lys Tyr Thr Ile Thr Gln Lys Gln Asn Pro Leu Ile
225                 230                 235                 240

Thr Asn Ile Arg Gly Thr Asn Ile Glu Glu Phe Leu Thr Phe Gly Gly
                245                 250                 255

Thr Asp Leu Asn Ile Ile Thr Ser Ala Gln Ser Asn Asp Ile Tyr Thr
            260                 265                 270

Asn Leu Leu Ala Asp Tyr Lys Lys Ile Ala Ser Lys Leu Ser Lys Val
            275                 280                 285

Gln Val Ser Asn Pro Leu Leu Asn Pro Tyr Lys Asp Val Phe Glu Ala
    290                 295                 300

Lys Tyr Gly Leu Asp Lys Asp Ala Ser Gly Ile Tyr Ser Val Asn Ile
305                 310                 315                 320

Asn Lys Phe Asn Asp Ile Phe Lys Lys Leu Tyr Ser Phe Thr Glu Phe
                325                 330                 335

Asp Leu Arg Thr Lys Phe Gln Val Lys Ser Arg Gln Thr Tyr Ile Gly
            340                 345                 350

Gln Tyr Lys Tyr Phe Lys Leu Ser Asn Leu Leu Asn Asp Ser Ile Tyr
            355                 360                 365

Asn Ile Ser Glu Gly Tyr Asn Ile Asn Asn Leu Lys Val Asn Phe Arg
    370                 375                 380

Gly Gln Asn Ala Asn Leu Asn Pro Arg Ile Ile Thr Pro Ile Thr Gly
385                 390                 395                 400

Arg Gly Leu Val Lys Lys Ile Ile Arg Phe Cys Lys Asn Ile Val Ser
                405                 410                 415

Val Lys Gly Ile Arg Lys Ser Ile Cys Ile Glu Ile Asn Asn Gly Glu
            420                 425                 430

Leu Phe Phe Val Ala Ser Glu Asn Ser Tyr Asn Asp Asp Asn Ile Asn
            435                 440                 445

Thr Pro Lys Glu Ile Asp Asp Thr Val Thr Ser Asn Asn Asn Tyr Glu
    450                 455                 460

Asn Asp Leu Asp Gln Val Ile Leu Asn Phe Asn Ser Glu Ser Ala Pro
465                 470                 475                 480
```

```
Gly Leu Ser Asp Glu Lys Leu Asn Leu Thr Ile Gln Asn Asp Ala Tyr
            485                 490                 495
Ile Pro Lys Tyr Asp Ser Asn Gly Thr Ser Asp Ile Glu Gln His Asp
        500                 505                 510
Val Asn Glu Leu Asn Val Phe Phe Tyr Leu Asp Ala Gln Lys Val Pro
            515                 520                 525
Glu Gly Glu Asn Asn Val Asn Leu Thr Ser Ser Ile Asp Thr Ala Leu
        530                 535                 540
Leu Glu Gln Pro Lys Ile Tyr Thr Phe Phe Ser Ser Glu Phe Ile Asn
545                 550                 555                 560
Asn Val Asn Lys Pro Val Gln Ala Ala Leu Phe Val Ser Trp Ile Gln
                565                 570                 575
Gln Val Leu Val Asp Phe Thr Thr Glu Ala Asn Gln Lys Ser Thr Val
            580                 585                 590
Asp Lys Ile Ala Asp Ile Ser Ile Val Val Pro Tyr Ile Gly Leu Ala
        595                 600                 605
Leu Asn Ile Gly Asn Glu Ala Gln Lys Gly Asn Phe Lys Asp Ala Leu
        610                 615                 620
Glu Leu Leu Gly Ala Gly Ile Leu Leu Glu Phe Glu Pro Glu Leu Leu
625                 630                 635                 640
Ile Pro Thr Ile Leu Val Phe Thr Ile Lys Ser Phe Leu Gly Ser Ser
            645                 650                 655
Asp Asn Lys Asn Lys Val Ile Lys Ala Ile Asn Asn Ala Leu Lys Glu
            660                 665                 670
Arg Asp Glu Lys Trp Lys Glu Val Tyr Ser Phe Ile Val Ser Asn Trp
        675                 680                 685
Met Thr Lys Ile Asn Thr Gln Phe Asn Lys Arg Lys Glu Gln Met Tyr
        690                 695                 700
Gln Ala Leu Gln Asn Gln Val Asn Ala Ile Lys Thr Ile Ile Glu Ser
705                 710                 715                 720
Lys Tyr Asn Ser Tyr Thr Leu Glu Glu Lys Asn Glu Leu Thr Asn Lys
                725                 730                 735
Tyr Asp Ile Lys Gln Ile Glu Asn Glu Leu Asn Gln Lys Val Ser Ile
            740                 745                 750
Ala Met Asn Asn Ile Asp Arg Phe Leu Thr Glu Ser Ser Ile Ser Tyr
        755                 760                 765
Leu Met Lys Ile Ile Asn Glu Val Lys Ile Asn Lys Leu Arg Glu Tyr
        770                 775                 780
Asp Glu Asn Val Lys Thr Tyr Leu Leu Asn Tyr Ile Ile Gln His Gly
785                 790                 795                 800
Ser Ile Leu Gly Glu Ser Gln Gln Glu Leu Asn Ser Met Val Thr Asp
                805                 810                 815
Thr Leu Asn Asn Ser Ile Pro Phe Lys Leu Ser Ser Tyr Thr Asp Asp
            820                 825                 830
Lys Ile Leu Ile Ser Tyr Phe Asn Lys Phe Phe Lys Arg Ile Lys Ser
        835                 840                 845
Ser Ser Val Leu Asn Met Arg Tyr Lys Asn Asp Lys Tyr Val Asp Thr
        850                 855                 860
Ser Gly Tyr Asp Ser Asn Ile Asn Ile Asn Gly Asp Val Tyr Lys Tyr
865                 870                 875                 880
Pro Thr Asn Lys Asn Gln Phe Gly Ile Tyr Asn Asp Lys Leu Ser Glu
                885                 890                 895
Val Asn Ile Ser Gln Asn Asp Tyr Ile Ile Tyr Asp Asn Lys Tyr Lys
```

```
                        900             905             910
Asn Phe Ser Ile Ser Phe Trp Val Arg Ile Pro Asn Tyr Asp Asn Lys
            915                 920                 925

Ile Val Asn Val Asn Asn Glu Tyr Thr Ile Ile Asn Cys Met Arg Asp
            930                 935                 940

Asn Asn Ser Gly Trp Lys Val Ser Leu Asn His Asn Glu Ile Ile Trp
945                 950                 955                 960

Thr Phe Glu Asp Asn Arg Gly Ile Asn Gln Lys Leu Ala Phe Asn Tyr
            965                 970                 975

Gly Asn Ala Asn Gly Ile Ser Asp Tyr Ile Asn Lys Trp Ile Phe Val
            980                 985                 990

Thr Ile Thr Asn Asp Arg Leu Gly Asp Ser Lys Leu Tyr Ile Asn Gly
            995                 1000                1005

Asn Leu Ile Asp Gln Lys Ser Ile Leu Asn Leu Gly Asn Ile His Val
        1010                1015                1020

Ser Asp Asn Ile Leu Phe Lys Ile Val Asn Cys Ser Tyr Thr Arg Tyr
1025                1030                1035                1040

Ile Gly Ile Arg Tyr Phe Asn Ile Phe Asp Lys Glu Leu Asp Glu Thr
            1045                1050                1055

Glu Ile Gln Thr Leu Tyr Ser Asn Glu
        1060                1065

<210> SEQ ID NO 11
<211> LENGTH: 844
<212> TYPE: PRT
<213> ORGANISM: Clostridium butyricum

<400> SEQUENCE: 11

Pro Thr Ile Asn Ser Phe Asn Tyr Asn Asp Pro Val Asn Asn Arg Thr
1               5                   10                  15

Ile Leu Tyr Ile Lys Pro Gly Gly Ser Gln Gln Phe Tyr Lys Ser Phe
            20                  25                  30

Asn Ile Met Lys Asn Ile Trp Ile Ile Pro Glu Arg Asn Val Ile Gly
        35                  40                  45

Thr Ile Pro Gln Asp Phe Leu Pro Pro Thr Ser Leu Lys Asn Gly Asp
    50                  55                  60

Ser Ser Tyr Tyr Asp Pro Asn Tyr Leu Gln Ser Asp Gln Glu Lys Asp
65                  70                  75                  80

Lys Phe Leu Lys Ile Val Thr Lys Ile Phe Asn Arg Ile Asn Asp Asn
            85                  90                  95

Leu Ser Gly Arg Ile Leu Leu Glu Glu Leu Ser Lys Ala Asn Pro Tyr
        100                 105                 110

Leu Gly Asn Asp Asn Thr Pro Asp Gly Asp Phe Ile Ile Asn Asp Ala
            115                 120                 125

Ser Ala Val Pro Ile Gln Phe Ser Asn Gly Ser Gln Ser Ile Leu Leu
    130                 135                 140

Pro Asn Val Ile Ile Met Gly Ala Glu Pro Asp Leu Phe Glu Thr Asn
145                 150                 155                 160

Ser Ser Asn Ile Ser Leu Arg Asn Asn Tyr Met Pro Ser Asn His Gly
            165                 170                 175

Phe Gly Ser Ile Ala Ile Val Thr Phe Ser Pro Glu Tyr Ser Phe Arg
        180                 185                 190

Phe Lys Asp Asn Ser Met Asn Glu Phe Ile Gln Asp Pro Ala Leu Thr
            195                 200                 205

Leu Met His Glu Leu Ile His Ser Leu His Gly Leu Tyr Gly Ala Lys
```

-continued

```
            210                 215                 220
Gly Ile Thr Thr Lys Tyr Thr Ile Thr Gln Lys Gln Asn Pro Leu Ile
225                 230                 235                 240

Thr Asn Ile Arg Gly Thr Asn Ile Glu Glu Phe Leu Thr Phe Gly Gly
                    245                 250                 255

Thr Asp Leu Asn Ile Ile Thr Ser Ala Gln Ser Asn Asp Ile Tyr Thr
                260                 265                 270

Asn Leu Leu Ala Asp Tyr Lys Lys Ile Ala Ser Lys Leu Ser Lys Val
                275                 280                 285

Gln Val Ser Asn Pro Leu Leu Asn Pro Tyr Lys Asp Val Phe Glu Ala
            290                 295                 300

Lys Tyr Gly Leu Asp Lys Asp Ala Ser Gly Ile Tyr Ser Val Asn Ile
305                 310                 315                 320

Asn Lys Phe Asn Asp Ile Phe Lys Lys Leu Tyr Ser Phe Thr Glu Phe
                    325                 330                 335

Asp Leu Ala Thr Lys Phe Gln Val Lys Ser Arg Gln Thr Tyr Ile Gly
                340                 345                 350

Gln Tyr Lys Tyr Phe Lys Leu Ser Asn Leu Leu Asn Asp Ser Ile Tyr
                355                 360                 365

Asn Ile Ser Glu Gly Tyr Asn Ile Asn Asn Leu Lys Val Asn Phe Arg
370                 375                 380

Gly Gln Asn Ala Asn Leu Asn Pro Arg Ile Ile Thr Pro Ile Thr Gly
385                 390                 395                 400

Arg Gly Leu Val Lys Lys Ile Ile Arg Phe Cys Lys Asn Ile Val Ser
                    405                 410                 415

Val Lys Gly Ile Arg Lys Ser Ile Cys Ile Glu Ile Asn Asn Gly Glu
                420                 425                 430

Leu Phe Phe Val Ala Ser Glu Asn Ser Tyr Asn Asp Asp Asn Ile Asn
                435                 440                 445

Thr Pro Lys Glu Ile Asp Asp Thr Val Thr Ser Asn Asn Asn Tyr Glu
            450                 455                 460

Asn Asp Leu Asp Gln Val Ile Leu Asn Phe Asn Ser Glu Ser Ala Pro
465                 470                 475                 480

Gly Leu Ser Asp Glu Lys Leu Asn Leu Thr Ile Gln Asn Asp Ala Tyr
                    485                 490                 495

Ile Pro Lys Tyr Asp Ser Asn Gly Thr Ser Asp Ile Glu Gln His Asp
                500                 505                 510

Val Asn Glu Leu Asn Val Phe Phe Tyr Leu Asp Ala Gln Lys Val Pro
                515                 520                 525

Glu Gly Glu Asn Asn Val Asn Leu Thr Ser Ser Ile Asp Thr Ala Leu
            530                 535                 540

Leu Glu Gln Pro Lys Ile Tyr Thr Phe Phe Ser Ser Glu Phe Ile Asn
545                 550                 555                 560

Asn Val Asn Lys Pro Val Gln Ala Ala Leu Phe Val Gly Trp Ile Gln
                    565                 570                 575

Gln Val Leu Val Asp Phe Thr Thr Glu Ala Asn Gln Lys Ser Thr Val
                580                 585                 590

Asp Lys Ile Ala Asp Ile Ser Ile Val Val Pro Tyr Ile Gly Leu Ala
                595                 600                 605

Leu Asn Ile Gly Asn Glu Ala Gln Lys Gly Asn Phe Lys Asp Ala Leu
            610                 615                 620

Glu Leu Leu Gly Ala Gly Ile Leu Leu Glu Phe Glu Pro Glu Leu Leu
625                 630                 635                 640
```

```
Ile Pro Thr Ile Leu Val Phe Thr Ile Lys Ser Phe Leu Gly Ser Ser
                645                 650                 655

Asp Asn Lys Asn Lys Val Ile Lys Ala Ile Asn Asn Ala Leu Lys Glu
            660                 665                 670

Arg Asp Glu Lys Trp Lys Glu Val Tyr Ser Phe Ile Val Ser Asn Trp
        675                 680                 685

Met Thr Lys Ile Asn Thr Gln Phe Asn Lys Arg Lys Glu Gln Met Tyr
    690                 695                 700

Gln Ala Leu Gln Asn Gln Val Asn Ala Leu Lys Ala Ile Ile Glu Ser
705                 710                 715                 720

Lys Tyr Asn Ser Tyr Thr Leu Glu Glu Lys Asn Glu Leu Thr Asn Lys
                725                 730                 735

Tyr Asp Ile Glu Gln Ile Glu Asn Glu Leu Asn Gln Lys Val Ser Ile
            740                 745                 750

Ala Met Asn Asn Ile Asp Arg Phe Leu Thr Glu Ser Ser Ile Ser Tyr
        755                 760                 765

Leu Met Lys Leu Ile Asn Glu Val Lys Ile Asn Lys Leu Arg Glu Tyr
    770                 775                 780

Asp Glu Asn Val Lys Thr Tyr Leu Leu Asp Tyr Ile Ile Lys His Gly
785                 790                 795                 800

Ser Ile Leu Gly Glu Ser Gln Gln Leu Asn Ser Met Val Ile Asp
                805                 810                 815

Thr Leu Asn Asn Ser Ile Pro Phe Lys Leu Ser Ser Tyr Thr Asp Asp
                820                 825                 830

Lys Ile Leu Ile Ser Tyr Phe Asn Lys Phe Phe Lys
                835                 840
```

<210> SEQ ID NO 12
<211> LENGTH: 844
<212> TYPE: PRT
<213> ORGANISM: Clostridium butyricum

<400> SEQUENCE: 12

```
Pro Thr Ile Asn Ser Phe Asn Tyr Asn Asp Pro Val Asn Asn Arg Thr
  1               5                  10                  15

Ile Leu Tyr Ile Lys Pro Gly Gly Ser Gln Gln Phe Tyr Lys Ser Phe
                20                  25                  30

Asn Ile Met Lys Asn Ile Trp Ile Ile Pro Glu Arg Asn Val Ile Gly
            35                  40                  45

Thr Ile Pro Gln Asp Phe Leu Pro Pro Thr Ser Leu Lys Asn Gly Asp
        50                  55                  60

Ser Ser Tyr Tyr Asp Pro Asn Tyr Leu Gln Ser Asp Gln Glu Lys Asp
65                  70                  75                  80

Lys Phe Leu Lys Ile Val Thr Lys Ile Phe Asn Arg Ile Asn Asp Asn
                85                  90                  95

Leu Ser Gly Arg Ile Leu Leu Glu Glu Leu Ser Lys Ala Asn Pro Tyr
            100                 105                 110

Leu Gly Asn Asp Asn Thr Pro Asp Gly Asp Phe Ile Ile Asn Asp Ala
        115                 120                 125

Ser Ala Val Pro Ile Gln Phe Ser Asn Gly Ser Gln Ser Ile Leu Leu
130                 135                 140

Pro Asn Val Ile Ile Met Gly Ala Glu Pro Asp Leu Phe Glu Thr Asn
145                 150                 155                 160

Ser Ser Asn Ile Ser Leu Arg Asn Asn Tyr Met Pro Ser Asn His Gly
                165                 170                 175
```

-continued

Phe Gly Ser Ile Ala Ile Val Thr Phe Ser Pro Glu Tyr Ser Phe Arg
            180                 185                 190

Phe Lys Asp Asn Ser Met Asn Glu Phe Ile Gln Asp Pro Ala Leu Thr
        195                 200                 205

Leu Met His Gln Leu Ile Tyr Ser Leu His Gly Leu Tyr Gly Ala Lys
    210                 215                 220

Gly Ile Thr Thr Lys Tyr Thr Ile Thr Gln Lys Gln Asn Pro Leu Ile
225                 230                 235                 240

Thr Asn Ile Arg Gly Thr Asn Ile Glu Glu Phe Leu Thr Phe Gly Gly
                245                 250                 255

Thr Asp Leu Asn Ile Ile Thr Ser Ala Gln Ser Asn Asp Ile Tyr Thr
            260                 265                 270

Asn Leu Leu Ala Asp Tyr Lys Lys Ile Ala Ser Lys Leu Ser Lys Val
        275                 280                 285

Gln Val Ser Asn Pro Leu Leu Asn Pro Tyr Lys Asp Val Phe Glu Ala
    290                 295                 300

Lys Tyr Gly Leu Asp Lys Asp Ala Ser Gly Ile Tyr Ser Val Asn Ile
305                 310                 315                 320

Asn Lys Phe Asn Asp Ile Phe Lys Lys Leu Tyr Ser Phe Thr Glu Phe
                325                 330                 335

Asp Leu Ala Thr Lys Phe Gln Val Lys Ser Arg Gln Thr Tyr Ile Gly
            340                 345                 350

Gln Tyr Lys Tyr Phe Lys Leu Ser Asn Leu Leu Asn Asp Ser Ile Tyr
        355                 360                 365

Asn Ile Ser Glu Gly Tyr Asn Ile Asn Asn Leu Lys Val Asn Phe Arg
    370                 375                 380

Gly Gln Asn Ala Asn Leu Asn Pro Arg Ile Ile Thr Pro Ile Thr Gly
385                 390                 395                 400

Arg Gly Leu Val Lys Lys Ile Arg Phe Cys Lys Asn Ile Val Ser
                405                 410                 415

Val Lys Gly Ile Arg Lys Ser Ile Cys Ile Glu Ile Asn Asn Gly Glu
            420                 425                 430

Leu Phe Phe Val Ala Ser Glu Asn Ser Tyr Asn Asp Asn Ile Asn
        435                 440                 445

Thr Pro Lys Glu Ile Asp Asp Thr Val Thr Ser Asn Asn Asn Tyr Glu
    450                 455                 460

Asn Asp Leu Asp Gln Val Ile Leu Asn Phe Asn Ser Glu Ser Ala Pro
465                 470                 475                 480

Gly Leu Ser Asp Glu Lys Leu Asn Leu Thr Ile Gln Asn Asp Ala Tyr
                485                 490                 495

Ile Pro Lys Tyr Asp Ser Asn Gly Thr Ser Asp Ile Glu Gln His Asp
            500                 505                 510

Val Asn Glu Leu Asn Val Phe Phe Tyr Leu Asp Ala Gln Lys Val Pro
        515                 520                 525

Glu Gly Glu Asn Asn Val Asn Leu Thr Ser Ser Ile Asp Thr Ala Leu
    530                 535                 540

Leu Glu Gln Pro Lys Ile Tyr Thr Phe Phe Ser Ser Glu Phe Ile Asn
545                 550                 555                 560

Asn Val Asn Lys Pro Val Gln Ala Ala Leu Phe Val Gly Trp Ile Gln
                565                 570                 575

Gln Val Leu Val Asp Phe Thr Thr Glu Ala Asn Gln Lys Ser Thr Val
            580                 585                 590

Asp Lys Ile Ala Asp Ile Ser Ile Val Val Pro Tyr Ile Gly Leu Ala
        595                 600                 605

```
Leu Asn Ile Gly Asn Glu Ala Gln Lys Gly Asn Phe Lys Asp Ala Leu
        610                 615                 620

Glu Leu Leu Gly Ala Gly Ile Leu Leu Glu Phe Glu Pro Glu Leu Leu
625                 630                 635                 640

Ile Pro Thr Ile Leu Val Phe Thr Ile Lys Ser Phe Leu Gly Ser Ser
                645                 650                 655

Asp Asn Lys Asn Lys Val Ile Lys Ala Ile Asn Asn Ala Leu Lys Glu
            660                 665                 670

Arg Asp Glu Lys Trp Lys Glu Val Tyr Ser Phe Ile Val Ser Asn Trp
        675                 680                 685

Met Thr Lys Ile Asn Thr Gln Phe Asn Lys Arg Lys Glu Gln Met Tyr
690                 695                 700

Gln Ala Leu Gln Asn Gln Val Asn Ala Leu Lys Ala Ile Ile Glu Ser
705                 710                 715                 720

Lys Tyr Asn Ser Tyr Thr Leu Glu Glu Lys Asn Glu Leu Thr Asn Lys
                725                 730                 735

Tyr Asp Ile Glu Gln Ile Glu Asn Glu Leu Asn Gln Lys Val Ser Ile
            740                 745                 750

Ala Met Asn Asn Ile Asp Arg Phe Leu Thr Glu Ser Ser Ile Ser Tyr
        755                 760                 765

Leu Met Lys Leu Ile Asn Glu Val Lys Ile Asn Lys Leu Arg Glu Tyr
770                 775                 780

Asp Glu Asn Val Lys Thr Tyr Leu Leu Asp Tyr Ile Ile Lys His Gly
785                 790                 795                 800

Ser Ile Leu Gly Glu Ser Gln Gln Glu Leu Asn Ser Met Val Ile Asp
                805                 810                 815

Thr Leu Asn Asn Ser Ile Pro Phe Lys Leu Ser Ser Tyr Thr Asp Asp
            820                 825                 830

Lys Ile Leu Ile Ser Tyr Phe Asn Lys Phe Phe Lys
        835                 840

<210> SEQ ID NO 13
<211> LENGTH: 1250
<212> TYPE: PRT
<213> ORGANISM: Clostridium butyricum

<400> SEQUENCE: 13

Pro Thr Ile Asn Ser Phe Asn Tyr Asn Asp Pro Val Asn Asn Arg Thr
1               5                   10                  15

Ile Leu Tyr Ile Lys Pro Gly Gly Ser Gln Gln Phe Tyr Lys Ser Phe
            20                  25                  30

Asn Ile Met Lys Asn Ile Trp Ile Ile Pro Glu Arg Asn Val Ile Gly
        35                  40                  45

Thr Ile Pro Gln Asp Phe Leu Pro Pro Thr Ser Leu Lys Asn Gly Asp
    50                  55                  60

Ser Ser Tyr Tyr Asp Pro Asn Tyr Leu Gln Ser Asp Gln Glu Lys Asp
65                  70                  75                  80

Lys Phe Leu Lys Ile Val Thr Lys Ile Phe Asn Arg Ile Asn Asp Asn
                85                  90                  95

Leu Ser Gly Arg Ile Leu Leu Glu Glu Leu Ser Lys Ala Asn Pro Tyr
            100                 105                 110

Leu Gly Asn Asp Asn Thr Pro Asp Gly Asp Phe Ile Ile Asn Asp Ala
        115                 120                 125

Ser Ala Val Pro Ile Gln Phe Ser Asn Gly Ser Gln Ser Ile Leu Leu
    130                 135                 140
```

```
Pro Asn Val Ile Ile Met Gly Ala Glu Pro Asp Leu Phe Glu Thr Asn
145                 150                 155                 160

Ser Ser Asn Ile Ser Leu Arg Asn Asn Tyr Met Pro Ser Asn His Gly
            165                 170                 175

Phe Gly Ser Ile Ala Ile Val Thr Phe Ser Pro Glu Tyr Ser Phe Arg
            180                 185                 190

Phe Lys Asp Asn Ser Met Asn Glu Phe Ile Gln Asp Pro Ala Leu Thr
            195                 200                 205

Leu Met His Gln Leu Ile Tyr Ser Leu His Gly Leu Tyr Gly Ala Lys
210                 215                 220

Gly Ile Thr Thr Lys Tyr Thr Ile Thr Gln Lys Asn Pro Leu Ile
225                 230                 235                 240

Thr Asn Ile Arg Gly Thr Asn Ile Glu Glu Phe Leu Thr Phe Gly Gly
            245                 250                 255

Thr Asp Leu Asn Ile Ile Thr Ser Ala Gln Ser Asn Asp Ile Tyr Thr
            260                 265                 270

Asn Leu Leu Ala Asp Tyr Lys Lys Ile Ala Ser Lys Leu Ser Lys Val
            275                 280                 285

Gln Val Ser Asn Pro Leu Leu Asn Pro Tyr Lys Asp Val Phe Glu Ala
290                 295                 300

Lys Tyr Gly Leu Asp Lys Asp Ala Ser Gly Ile Tyr Ser Val Asn Ile
305                 310                 315                 320

Asn Lys Phe Asn Asp Ile Phe Lys Lys Leu Tyr Ser Phe Thr Glu Phe
            325                 330                 335

Asp Leu Ala Thr Lys Phe Gln Val Lys Ser Arg Gln Thr Tyr Ile Gly
            340                 345                 350

Gln Tyr Lys Tyr Phe Lys Leu Ser Asn Leu Leu Asn Asp Ser Ile Tyr
            355                 360                 365

Asn Ile Ser Glu Gly Tyr Asn Ile Asn Asn Leu Lys Val Asn Phe Arg
370                 375                 380

Gly Gln Asn Ala Asn Leu Asn Pro Arg Ile Ile Thr Pro Ile Thr Gly
385                 390                 395                 400

Arg Gly Leu Val Lys Lys Ile Ile Arg Phe Cys Lys Asn Ile Val Ser
            405                 410                 415

Val Lys Gly Ile Arg Lys Ser Ile Cys Ile Glu Ile Asn Asn Gly Glu
            420                 425                 430

Leu Phe Phe Val Ala Ser Glu Asn Ser Tyr Asn Asp Asp Asn Ile Asn
            435                 440                 445

Thr Pro Lys Glu Ile Asp Asp Thr Val Thr Ser Asn Asn Asn Tyr Glu
450                 455                 460

Asn Asp Leu Asp Gln Val Ile Leu Asn Phe Asn Ser Glu Ser Ala Pro
465                 470                 475                 480

Gly Leu Ser Asp Glu Lys Leu Asn Leu Thr Ile Gln Asn Asp Ala Tyr
            485                 490                 495

Ile Pro Lys Tyr Asp Ser Asn Gly Thr Ser Asp Ile Glu Gln His Asp
            500                 505                 510

Val Asn Glu Leu Asn Val Phe Phe Tyr Leu Asp Ala Gln Lys Val Pro
            515                 520                 525

Glu Gly Glu Asn Asn Val Asn Leu Thr Ser Ser Ile Asp Thr Ala Leu
530                 535                 540

Leu Glu Gln Pro Lys Ile Tyr Thr Phe Phe Ser Ser Glu Phe Ile Asn
545                 550                 555                 560

Asn Val Asn Lys Pro Val Gln Ala Ala Leu Phe Val Gly Trp Ile Gln
```

```
                565                 570                 575
Gln Val Leu Val Asp Phe Thr Thr Glu Ala Asn Gln Lys Ser Thr Val
            580                 585                 590

Asp Lys Ile Ala Asp Ile Ser Ile Val Val Pro Tyr Ile Gly Leu Ala
            595                 600                 605

Leu Asn Ile Gly Asn Glu Ala Gln Lys Gly Asn Phe Lys Asp Ala Leu
            610                 615                 620

Glu Leu Leu Gly Ala Gly Ile Leu Leu Glu Phe Glu Pro Glu Leu Leu
625                 630                 635                 640

Ile Pro Thr Ile Leu Val Phe Thr Ile Lys Ser Phe Leu Gly Ser Ser
            645                 650                 655

Asp Asn Lys Asn Lys Val Ile Lys Ala Ile Asn Asn Ala Leu Lys Glu
            660                 665                 670

Arg Asp Glu Lys Trp Lys Glu Val Tyr Ser Phe Ile Val Ser Asn Trp
            675                 680                 685

Met Thr Lys Ile Asn Thr Gln Phe Asn Lys Arg Lys Glu Gln Met Tyr
            690                 695                 700

Gln Ala Leu Gln Asn Gln Val Asn Ala Leu Lys Ala Ile Ile Glu Ser
705                 710                 715                 720

Lys Tyr Asn Ser Tyr Thr Leu Glu Glu Lys Asn Glu Leu Thr Asn Lys
            725                 730                 735

Tyr Asp Ile Glu Gln Ile Glu Asn Glu Leu Asn Gln Lys Val Ser Ile
            740                 745                 750

Ala Met Asn Asn Ile Asp Arg Phe Leu Thr Glu Ser Ser Ile Ser Tyr
            755                 760                 765

Leu Met Lys Leu Ile Asn Glu Val Lys Ile Asn Lys Leu Arg Glu Tyr
            770                 775                 780

Asp Glu Asn Val Lys Thr Tyr Leu Leu Asp Tyr Ile Ile Lys His Gly
785                 790                 795                 800

Ser Ile Leu Gly Glu Ser Gln Gln Glu Leu Asn Ser Met Val Ile Asp
            805                 810                 815

Thr Leu Asn Asn Ser Ile Pro Phe Lys Leu Ser Ser Tyr Thr Asp Asp
            820                 825                 830

Lys Ile Leu Ile Ser Tyr Phe Asn Lys Phe Phe Lys Arg Ile Lys Ser
            835                 840                 845

Ser Ser Val Leu Asn Met Arg Tyr Lys Asn Asp Lys Tyr Val Asp Thr
850                 855                 860

Ser Gly Tyr Asp Ser Asn Ile Asn Ile Asn Gly Asp Val Tyr Lys Tyr
865                 870                 875                 880

Pro Thr Asn Lys Asn Gln Phe Gly Ile Tyr Asn Asp Lys Leu Ser Glu
            885                 890                 895

Val Asn Ile Ser Gln Asn Asp Tyr Ile Ile Tyr Asp Asn Lys Tyr Lys
            900                 905                 910

Asn Phe Ser Ile Ser Phe Trp Val Arg Ile Pro Asn Tyr Asp Asn Lys
            915                 920                 925

Ile Val Asn Val Asn Asn Glu Tyr Thr Ile Ile Asn Cys Met Arg Asp
            930                 935                 940

Asn Asn Ser Gly Trp Lys Val Ser Leu Asn His Asn Glu Ile Ile Trp
945                 950                 955                 960

Thr Leu Gln Asp Asn Ser Gly Ile Asn Gln Lys Leu Ala Phe Asn Tyr
            965                 970                 975

Gly Asn Ala Asn Gly Ile Ser Asp Tyr Ile Asn Lys Trp Ile Phe Val
            980                 985                 990
```

```
Thr Ile Thr Asn Asp Arg Leu Gly Asp Ser Lys Leu Tyr Ile Asn Gly
        995                 1000                1005

Asn Leu Ile Asp Lys Lys Ser Ile Leu Asn Leu Gly Asn Ile His Val
    1010                1015                1020

Ser Asp Asn Ile Leu Phe Lys Ile Val Asn Cys Ser Tyr Thr Arg Tyr
1025                1030                1035                1040

Ile Gly Ile Arg Tyr Phe Asn Ile Phe Asp Lys Glu Leu Asp Glu Thr
        1045                1050                1055

Glu Ile Gln Thr Leu Tyr Asn Asn Glu Pro Asn Ala Asn Ile Leu Lys
        1060                1065                1070

Asp Phe Trp Gly Asn Tyr Leu Leu Tyr Asp Lys Glu Tyr Tyr Leu Leu
        1075                1080                1085

Asn Val Leu Lys Pro Asn Asn Phe Ile Asn Arg Arg Thr Asp Ser Thr
        1090                1095                1100

Leu Ser Ile Asn Asn Ile Arg Ser Thr Ile Leu Leu Ala Asn Arg Leu
1105                1110                1115                1120

Tyr Ser Gly Ile Lys Val Lys Ile Gln Arg Val Asn Asn Ser Ser Thr
        1125                1130                1135

Asn Asp Asn Leu Val Arg Lys Asn Asp Gln Val Tyr Ile Asn Phe Val
        1140                1145                1150

Ala Ser Lys Thr His Leu Leu Pro Leu Tyr Ala Asp Thr Ala Thr Thr
        1155                1160                1165

Asn Lys Glu Lys Thr Ile Lys Ile Ser Ser Ser Gly Asn Arg Phe Asn
        1170                1175                1180

Gln Val Val Val Met Asn Ser Val Gly Asn Cys Thr Met Asn Phe Lys
1185                1190                1195                1200

Asn Asn Asn Gly Asn Asn Ile Gly Leu Leu Gly Phe Lys Ala Asp Thr
        1205                1210                1215

Val Val Ala Ser Thr Leu Phe Tyr Thr His Met Arg Asp Asn Thr Asn
        1220                1225                1230

Ser Asn Gly Phe Phe Trp Asn Phe Ile Ser Glu Glu His Gly Trp Gln
        1235                1240                1245

Glu Lys
    1250

<210> SEQ ID NO 14
<211> LENGTH: 1065
<212> TYPE: PRT
<213> ORGANISM: Clostridium butyricum

<400> SEQUENCE: 14

Pro Lys Ile Asn Ser Phe Asn Tyr Asn Asp Pro Val Asn Asp Arg Thr
1               5                   10                  15

Ile Leu Tyr Ile Lys Pro Gly Gly Ser Gln Glu Phe Tyr Lys Ser Phe
            20                  25                  30

Asn Ile Met Lys Asn Ile Trp Ile Ile Pro Glu Arg Asn Val Ile Gly
        35                  40                  45

Thr Thr Pro Gln Asp Phe His Pro Pro Thr Ser Leu Lys Asn Gly Asp
    50                  55                  60

Ser Ser Tyr Tyr Asp Pro Asn Tyr Leu Gln Ser Asp Glu Glu Lys Asp
65                  70                  75                  80

Arg Phe Leu Lys Ile Val Thr Lys Ile Phe Asn Arg Ile Asn Asn Asn
            85                  90                  95

Leu Ser Gly Gly Ile Leu Leu Glu Glu Leu Ser Lys Ala Asn Pro Tyr
            100                 105                 110
```

-continued

Leu Gly Asn Asp Asn Thr Pro Asp Asn Gln Phe His Ile Gly Asp Ala
        115                 120                 125

Ser Ala Val Glu Ile Lys Phe Ser Asn Gly Ser Gln Asp Ile Leu Leu
    130                 135                 140

Pro Asn Val Ile Ile Met Gly Ala Glu Pro Asp Leu Phe Glu Thr Asn
145                 150                 155                 160

Ser Ser Asn Ile Ser Leu Arg Asn Asn Tyr Met Pro Ser Asn His Arg
                165                 170                 175

Phe Gly Ser Ile Ala Ile Val Thr Phe Ser Pro Glu Tyr Ser Phe Arg
            180                 185                 190

Phe Asn Asp Asn Cys Met Asn Glu Phe Ile Gln Asp Pro Ala Leu Thr
        195                 200                 205

Leu Met His Gln Leu Ile Tyr Ser Leu His Gly Leu Tyr Gly Ala Lys
    210                 215                 220

Gly Ile Thr Thr Lys Tyr Thr Ile Thr Gln Lys Gln Asn Pro Leu Ile
225                 230                 235                 240

Thr Asn Ile Arg Gly Thr Asn Ile Glu Glu Phe Leu Thr Phe Gly Gly
                245                 250                 255

Thr Asp Leu Asn Ile Ile Thr Ser Ala Gln Ser Asn Asp Ile Tyr Thr
            260                 265                 270

Asn Leu Leu Ala Asp Tyr Lys Lys Ile Ala Ser Lys Leu Ser Lys Val
        275                 280                 285

Gln Val Ser Asn Pro Leu Leu Asn Pro Tyr Lys Asp Val Phe Glu Ala
    290                 295                 300

Lys Tyr Gly Leu Asp Lys Asp Ala Ser Gly Ile Tyr Ser Val Asn Ile
305                 310                 315                 320

Asn Lys Phe Asn Asp Ile Phe Lys Lys Leu Tyr Ser Phe Thr Glu Phe
                325                 330                 335

Asp Leu Arg Thr Lys Phe Gln Val Lys Ser Arg Gln Thr Tyr Ile Gly
            340                 345                 350

Gln Tyr Lys Tyr Phe Lys Leu Ser Asn Leu Leu Asn Asp Ser Ile Tyr
        355                 360                 365

Asn Ile Ser Glu Gly Tyr Asn Ile Asn Asn Leu Lys Val Asn Phe Arg
    370                 375                 380

Gly Gln Asn Ala Asn Leu Asn Pro Arg Ile Ile Thr Pro Ile Thr Gly
385                 390                 395                 400

Arg Gly Leu Val Lys Lys Ile Ile Arg Phe Cys Lys Asn Ile Val Ser
                405                 410                 415

Val Lys Gly Ile Arg Lys Ser Ile Cys Ile Glu Ile Asn Gly Glu
            420                 425                 430

Leu Phe Phe Val Ala Ser Glu Asn Ser Tyr Asn Asp Asp Asn Ile Asn
        435                 440                 445

Thr Pro Lys Glu Ile Asp Asp Thr Val Thr Ser Asn Asn Asn Tyr Glu
    450                 455                 460

Asn Asp Leu Asp Gln Val Ile Leu Asn Phe Asn Ser Glu Ser Ala Pro
465                 470                 475                 480

Gly Leu Ser Asp Glu Lys Leu Asn Leu Thr Ile Gln Asn Asp Ala Tyr
                485                 490                 495

Ile Pro Lys Tyr Asp Ser Asn Gly Thr Ser Asp Ile Glu Gln His Asp
            500                 505                 510

Val Asn Glu Leu Asn Val Phe Phe Tyr Leu Asp Ala Gln Lys Val Pro
        515                 520                 525

Glu Gly Glu Asn Asn Val Asn Leu Thr Ser Ser Ile Asp Thr Ala Leu
    530                 535                 540

```
Leu Glu Gln Pro Lys Ile Tyr Thr Phe Phe Ser Ser Glu Phe Ile Asn
545                 550                 555                 560

Asn Val Asn Lys Pro Val Gln Ala Ala Leu Phe Val Ser Trp Ile Gln
                565                 570                 575

Gln Val Leu Val Asp Phe Thr Thr Glu Ala Asn Gln Lys Ser Thr Val
            580                 585                 590

Asp Lys Ile Ala Asp Ile Ser Ile Val Val Pro Tyr Ile Gly Leu Ala
        595                 600                 605

Leu Asn Ile Gly Asn Glu Ala Gln Lys Gly Asn Phe Lys Asp Ala Leu
    610                 615                 620

Glu Leu Leu Gly Ala Gly Ile Leu Leu Glu Phe Glu Pro Glu Leu Leu
625                 630                 635                 640

Ile Pro Thr Ile Leu Val Phe Thr Ile Lys Ser Phe Leu Gly Ser Ser
                645                 650                 655

Asp Asn Lys Asn Lys Val Ile Lys Ala Ile Asn Asn Ala Leu Lys Glu
                660                 665                 670

Arg Asp Glu Lys Trp Lys Glu Val Tyr Ser Phe Ile Val Ser Asn Trp
            675                 680                 685

Met Thr Lys Ile Asn Thr Gln Phe Asn Lys Arg Lys Glu Gln Met Tyr
        690                 695                 700

Gln Ala Leu Gln Asn Gln Val Asn Ala Ile Lys Thr Ile Ile Glu Ser
705                 710                 715                 720

Lys Tyr Asn Ser Tyr Thr Leu Glu Glu Lys Asn Glu Leu Thr Asn Lys
                725                 730                 735

Tyr Asp Ile Lys Gln Ile Glu Asn Glu Leu Asn Gln Lys Val Ser Ile
                740                 745                 750

Ala Met Asn Asn Ile Asp Arg Phe Leu Thr Glu Ser Ser Ile Ser Tyr
            755                 760                 765

Leu Met Lys Ile Ile Asn Glu Val Lys Ile Asn Lys Leu Arg Glu Tyr
        770                 775                 780

Asp Glu Asn Val Lys Thr Tyr Leu Leu Asn Tyr Ile Ile Gln His Gly
785                 790                 795                 800

Ser Ile Leu Gly Glu Ser Gln Gln Glu Leu Asn Ser Met Val Thr Asp
                805                 810                 815

Thr Leu Asn Asn Ser Ile Pro Phe Lys Leu Ser Ser Tyr Thr Asp Asp
                820                 825                 830

Lys Ile Leu Ile Ser Tyr Phe Asn Lys Phe Phe Lys Arg Ile Lys Ser
            835                 840                 845

Ser Ser Val Leu Asn Met Arg Tyr Lys Asn Asp Lys Tyr Val Asp Thr
        850                 855                 860

Ser Gly Tyr Asp Ser Asn Ile Asn Ile Asn Gly Asp Val Tyr Lys Tyr
865                 870                 875                 880

Pro Thr Asn Lys Asn Gln Phe Gly Ile Tyr Asn Asp Lys Leu Ser Glu
                885                 890                 895

Val Asn Ile Ser Gln Asn Asp Tyr Ile Ile Tyr Asp Asn Lys Tyr Lys
                900                 905                 910

Asn Phe Ser Ile Ser Phe Trp Val Arg Ile Pro Asn Tyr Asp Asn Lys
            915                 920                 925

Ile Val Asn Val Asn Asn Glu Tyr Thr Ile Ile Asn Cys Met Arg Asp
        930                 935                 940

Asn Asn Ser Gly Trp Lys Val Ser Leu Asn His Asn Glu Ile Ile Trp
945                 950                 955                 960

Thr Phe Glu Asp Asn Arg Gly Ile Asn Gln Lys Leu Ala Phe Asn Tyr
```

-continued

```
                        965                 970                 975
Gly Asn Ala Asn Gly Ile Ser Asp Tyr Ile Asn Lys Trp Ile Phe Val
            980                 985                 990

Thr Ile Thr Asn Asp Arg Leu Gly Asp Ser Lys Leu Tyr Ile Asn Gly
        995                1000                1005

Asn Leu Ile Asp Gln Lys Ser Ile Leu Asn Leu Gly Asn Ile His Val
    1010                1015                1020

Ser Asp Asn Ile Leu Phe Lys Ile Val Asn Cys Ser Tyr Thr Arg Tyr
1025                1030                1035                1040

Ile Gly Ile Arg Tyr Phe Asn Ile Phe Asp Lys Glu Leu Asp Glu Thr
            1045                1050                1055

Glu Ile Gln Thr Leu Tyr Ser Asn Glu
        1060                1065
```